(12) United States Patent
Cecchetto

(10) Patent No.: US 11,925,539 B2
(45) Date of Patent: Mar. 12, 2024

(54) DISPOSABLE ABSORBENT ARTICLE

(71) Applicant: The Procter & Gamble Company, Cincinnati, OH (US)

(72) Inventor: Pietro Cecchetto, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 827 days.

(21) Appl. No.: 16/547,843

(22) Filed: Aug. 22, 2019

(65) Prior Publication Data
US 2020/0060882 A1 Feb. 27, 2020

Related U.S. Application Data

(60) Provisional application No. 62/720,952, filed on Aug. 22, 2018.

(51) Int. Cl.
*A61F 13/512* (2006.01)
*A61F 13/15* (2006.01)
*A61F 13/472* (2006.01)

(52) U.S. Cl.
CPC ...... *A61F 13/15731* (2013.01); *A61F 13/472* (2013.01); *A61F 13/5121* (2013.01); *A61F 13/5122* (2013.01); *A61F 13/5123* (2013.01)

(58) Field of Classification Search
CPC .............. A61F 13/5121; A61F 13/5122; A61F 13/5123; A61F 13/512
See application file for complete search history.

(56) References Cited

U.S. PATENT DOCUMENTS

| | | |
|---|---|---|
| 577,965 A | 3/1897 | Major |
| 2,068,456 A | 1/1937 | Hooper |
| 2,275,425 A | 3/1942 | Grabec |
| 2,404,758 A | 7/1946 | Teague et al. |
| 2,633,441 A | 3/1953 | Buttress |
| 2,699,208 A | 1/1955 | Schur |
| 2,748,863 A | 6/1956 | Benton |
| 2,924,863 A | 2/1960 | Chavannes |

(Continued)

FOREIGN PATENT DOCUMENTS

| BR | 200703778 | 7/2008 |
|---|---|---|
| CA | 2615680 A1 | 1/2007 |

(Continued)

OTHER PUBLICATIONS

15071M PCT Search Report and Written Opinion for PCT/US2019/047598 dated Nov. 22, 2019.

(Continued)

*Primary Examiner* — Jessica Arble
(74) *Attorney, Agent, or Firm* — Sarah M. DeCristofaro; George Henry Leal

(57) ABSTRACT

A material web having a film layer and a nonwoven layer, along with methods of making the material web, are described. The material web has a plurality of micro-deformations and a plurality of macro-deformations, each of the macro-deformations having a distal end, wherein a first portion of macro-deformations has an open or partially open distal end and wherein a second portion of macro-deformations has distal ends which are configured differently than the distal ends of the first portion, and wherein the material web forms a portion of the topsheet.

9 Claims, 26 Drawing Sheets

(56) References Cited

U.S. PATENT DOCUMENTS

| | | |
|---|---|---|
| 3,017,304 A | 1/1962 | Burgeni |
| 3,034,180 A | 5/1962 | Greiner et al. |
| 3,073,304 A | 1/1963 | Schaar |
| 3,081,500 A | 3/1963 | Griswold, et al. |
| 3,081,512 A | 3/1963 | Griswold |
| 3,097,787 A | 7/1963 | Schur |
| 3,137,893 A | 6/1964 | Gelpke |
| 3,243,488 A | 3/1966 | Hannauer, Jr. et al. |
| 3,355,974 A | 12/1967 | Carmichael |
| 3,466,358 A | 9/1969 | Muller |
| 3,496,259 A | 2/1970 | Guenther |
| 3,509,007 A | 4/1970 | Kalwaites |
| 3,511,740 A | 5/1970 | Sanders |
| 3,539,423 A | 11/1970 | Simison et al. |
| 3,542,634 A | 11/1970 | Such et al. |
| 3,549,742 A | 12/1970 | Benz |
| 3,566,726 A | 3/1971 | Politis |
| 3,579,763 A | 5/1971 | Sommer |
| 3,681,182 A | 8/1972 | Falwaites |
| 3,681,183 A | 8/1972 | Kalwaites |
| 3,684,284 A | 8/1972 | Tranfield |
| 3,695,270 A | 10/1972 | Dostal |
| 3,718,059 A | 2/1973 | Clayton |
| 3,760,671 A | 9/1973 | Jenkins |
| 3,881,987 A | 5/1975 | Benz |
| 3,949,127 A | 4/1976 | Ostermeier et al. |
| 3,965,906 A | 6/1976 | Karami |
| 3,994,771 A | 11/1976 | Morgan, Jr. |
| 4,035,881 A | 7/1977 | Zocher |
| 4,042,453 A | 8/1977 | Conway et al. |
| 4,135,021 A | 1/1979 | Patchell et al. |
| 4,189,344 A | 2/1980 | Busker |
| 4,211,743 A | 7/1980 | Kos |
| 4,244,683 A | 1/1981 | Rowland |
| 4,276,336 A | 6/1981 | Sabee |
| 4,300,981 A | 11/1981 | Carstens |
| 4,342,314 A | 8/1982 | Radel et al. |
| 4,379,799 A | 4/1983 | Holmes et al. |
| 4,397,644 A | 8/1983 | Matthews et al. |
| 4,422,837 A | 12/1983 | Rasmussen |
| 4,463,045 A | 7/1984 | Ahr et al. |
| 4,465,726 A | 8/1984 | Holmes et al. |
| 4,469,734 A | 9/1984 | Minto et al. |
| 4,514,345 A | 4/1985 | Johnson et al. |
| 4,528,239 A | 7/1985 | Trokhan |
| 4,529,480 A | 7/1985 | Trokhan |
| 4,588,630 A | 5/1986 | Shimalla |
| 4,609,518 A | 9/1986 | Curro et al. |
| 4,614,679 A | 9/1986 | Farrington, Jr. |
| 4,629,643 A | 12/1986 | Curro et al. |
| 4,695,422 A | 9/1987 | Curro et al. |
| 4,741,941 A | 5/1988 | Englebert et al. |
| 4,758,297 A | 7/1988 | Calligarich |
| 4,767,586 A | 8/1988 | Radwanski et al. |
| 4,781,962 A | 11/1988 | Zamarripa et al. |
| 4,798,604 A | 1/1989 | Carter |
| 4,820,294 A | 4/1989 | Morris |
| 4,840,829 A | 6/1989 | Suzuki et al. |
| 4,842,794 A | 6/1989 | Hovis et al. |
| 4,859,519 A | 8/1989 | Cabe, Jr. |
| 4,886,632 A | 12/1989 | Van Iten et al. |
| 4,935,087 A | 6/1990 | Gilman |
| 4,953,270 A | 9/1990 | Gilpatrick |
| 4,992,324 A | 2/1991 | Dube |
| 5,019,062 A | 5/1991 | Ryan et al. |
| 5,062,418 A | 11/1991 | Dyer et al. |
| 5,143,679 A | 9/1992 | Weber |
| 5,144,730 A | 9/1992 | Dilo |
| 5,151,077 A | 9/1992 | Cole, Jr. et al. |
| 5,165,979 A | 11/1992 | Watkins et al. |
| 5,171,238 A | 12/1992 | Kajander |
| 5,180,620 A | 1/1993 | Mende |
| 5,188,625 A | 2/1993 | Van Iten et al. |
| 5,223,319 A | 6/1993 | Cotton et al. |
| 5,242,435 A | 9/1993 | Murji |
| 5,242,632 A | 9/1993 | Mende |
| 5,328,565 A | 7/1994 | Rasch et al. |
| 5,382,245 A | 1/1995 | Thompson et al. |
| 5,383,870 A | 1/1995 | Takai et al. |
| 5,387,209 A | 2/1995 | Yamamoto et al. |
| 5,387,385 A | 2/1995 | Murji |
| 5,405,675 A | 4/1995 | Sawka |
| 5,414,914 A | 5/1995 | Suzuki et al. |
| 5,415,640 A | 5/1995 | Kirby et al. |
| 5,429,854 A | 7/1995 | Currie et al. |
| 5,437,653 A | 8/1995 | Gilman et al. |
| 5,470,326 A | 11/1995 | Dabi et al. |
| 5,503,715 A | 4/1996 | Trokhan et al. |
| 5,505,720 A | 4/1996 | Hujber |
| 5,508,080 A | 4/1996 | Sorimachi et al. |
| 5,518,801 A | 5/1996 | Chappell et al. |
| 5,533,991 A | 7/1996 | Kirby et al. |
| 5,534,326 A | 7/1996 | Trokhan et al. |
| 5,554,145 A | 9/1996 | Roe et al. |
| 5,560,794 A | 10/1996 | Currie et al. |
| 5,562,645 A | 10/1996 | Tanzer |
| 5,567,501 A | 10/1996 | Srinivasan et al. |
| D375,844 S | 11/1996 | Edwards et al. |
| 5,573,719 A | 11/1996 | Fitting |
| 5,575,874 A | 11/1996 | Griesbach, III et al. |
| 5,580,418 A | 12/1996 | Alikhan |
| 5,599,420 A | 2/1997 | Yeo et al. |
| 5,624,427 A | 4/1997 | Bergman et al. |
| 5,626,571 A | 5/1997 | Young et al. |
| 5,628,097 A | 5/1997 | Benson et al. |
| 5,634,915 A | 6/1997 | Oesterdahl |
| 5,637,194 A | 6/1997 | Ampulski et al. |
| 5,648,142 A | 7/1997 | Phillips |
| 5,656,119 A | 8/1997 | Srinivasan et al. |
| 5,658,639 A | 8/1997 | Curro et al. |
| 5,667,619 A | 9/1997 | Alikhan |
| 5,667,625 A | 9/1997 | Alikhan |
| 5,691,035 A | 11/1997 | Chappell |
| 5,700,255 A | 12/1997 | Curro et al. |
| 5,704,101 A | 1/1998 | Majors |
| 5,709,829 A | 1/1998 | Giacometti |
| 5,714,041 A | 2/1998 | Ayers et al. |
| 5,714,107 A | 2/1998 | Levy et al. |
| 5,723,087 A | 3/1998 | Chappell |
| 5,727,458 A | 3/1998 | Schulz |
| 5,743,776 A | 4/1998 | Igaue et al. |
| 5,743,999 A | 4/1998 | Kamps |
| 5,804,021 A | 9/1998 | Abuto et al. |
| 5,814,389 A | 9/1998 | Giacometti |
| 5,817,394 A | 10/1998 | Alikhan et al. |
| 5,841,107 A | 11/1998 | Riva |
| 5,846,636 A | 12/1998 | Ruppel |
| 5,858,504 A | 1/1999 | Fitting |
| 5,879,494 A | 3/1999 | Hoff et al. |
| 5,891,544 A | 4/1999 | Chappell |
| 5,895,623 A | 4/1999 | Trokhan et al. |
| 5,897,930 A | 4/1999 | Calhoun et al. |
| 5,900,122 A | 5/1999 | Huston |
| 5,906,710 A | 5/1999 | Trokhan |
| 5,914,084 A | 6/1999 | Benson et al. |
| 5,916,507 A | 6/1999 | Dabi |
| 5,916,661 A | 6/1999 | Benson et al. |
| 5,916,663 A | 6/1999 | Chappell |
| 5,919,177 A | 7/1999 | Georger et al. |
| 5,925,026 A | 7/1999 | Arteman et al. |
| 5,925,299 A | 7/1999 | Dierckes, Jr. et al. |
| 5,935,381 A | 8/1999 | Trokhan et al. |
| 5,964,742 A | 10/1999 | McCormack et al. |
| 5,968,029 A | 10/1999 | Chappell et al. |
| 5,986,167 A | 11/1999 | Arteman et al. |
| 5,993,432 A | 11/1999 | Lodge et al. |
| 5,998,693 A | 12/1999 | Zagame |
| 5,998,696 A | 12/1999 | Schone |
| 6,007,468 A | 12/1999 | Giacometti |
| 6,025,050 A | 2/2000 | Srinivasan et al. |
| 6,027,483 A | 2/2000 | Chappell |
| 6,039,555 A | 3/2000 | Tsuji et al. |
| 6,053,232 A | 4/2000 | Biagiotti |
| 6,074,524 A | 6/2000 | Wu |

(56) References Cited

U.S. PATENT DOCUMENTS

| | | |
|---|---|---|
| 6,080,276 A | 6/2000 | Burgess |
| 6,096,016 A | 8/2000 | Tsuji et al. |
| 6,106,928 A | 8/2000 | Laurent |
| 6,109,326 A | 8/2000 | Leakey |
| 6,114,263 A | 9/2000 | Benson et al. |
| 6,117,524 A | 9/2000 | Hisanaka et al. |
| 6,120,718 A | 9/2000 | Kotek et al. |
| 6,129,801 A | 10/2000 | Benson et al. |
| 6,136,146 A | 10/2000 | Phan et al. |
| 6,155,083 A | 12/2000 | Goeser et al. |
| 6,168,849 B1 | 1/2001 | Braverman et al. |
| 6,176,954 B1 | 1/2001 | Tsuji et al. |
| 6,247,914 B1 | 6/2001 | Lindquist et al. |
| D444,631 S | 7/2001 | Woodbridge et al. |
| 6,258,308 B1 | 7/2001 | Brady |
| 6,264,872 B1 | 7/2001 | Majors et al. |
| 6,287,407 B1 | 9/2001 | Stein et al. |
| 6,296,737 B1 | 10/2001 | Wu |
| 6,324,738 B1 | 12/2001 | Fleissner |
| 6,332,955 B1 | 12/2001 | Meschenmoser |
| 6,344,109 B1 | 2/2002 | Gross |
| 6,344,111 B1 | 2/2002 | Wilhelm |
| 6,355,200 B1 | 3/2002 | Schmidt |
| 6,368,539 B1 | 4/2002 | Greenfield |
| 6,383,431 B1 | 5/2002 | Dobrin |
| 6,383,441 B1 | 5/2002 | Takai |
| 6,395,122 B1 | 5/2002 | Hisanaka et al. |
| 6,395,211 B1 | 5/2002 | Dettmer et al. |
| 6,395,957 B1 | 5/2002 | Chen et al. |
| 6,398,895 B1 | 6/2002 | Stein et al. |
| 6,410,823 B1 | 6/2002 | Daley et al. |
| 6,420,625 B1 | 7/2002 | Jones et al. |
| 6,423,884 B1 | 7/2002 | Oehmen |
| 6,444,089 B1 | 9/2002 | Hollmark et al. |
| 6,451,718 B1 | 9/2002 | Yamada et al. |
| 6,452,064 B1 | 9/2002 | Thoren et al. |
| 6,454,905 B1 | 9/2002 | Hollmark et al. |
| 6,458,447 B1 | 10/2002 | Cabell |
| 6,464,831 B1 | 10/2002 | Trokhan et al. |
| D466,702 S | 12/2002 | Carlson et al. |
| 6,503,370 B2 | 1/2003 | Hollmark et al. |
| 6,506,329 B1 | 1/2003 | Curro |
| 6,533,898 B2 | 3/2003 | Gross |
| 6,537,936 B1 | 3/2003 | Busam et al. |
| 6,596,127 B2 | 7/2003 | Hollmark et al. |
| 6,599,612 B1 | 7/2003 | Gray |
| 6,610,904 B1 | 8/2003 | Thomas et al. |
| 6,620,485 B1 | 9/2003 | Benson et al. |
| 6,632,504 B1 | 10/2003 | Gillespie et al. |
| D481,872 S | 11/2003 | Hennel et al. |
| 6,647,549 B2 | 11/2003 | McDevitt et al. |
| 6,669,878 B2 | 12/2003 | Yamada et al. |
| 6,716,498 B2 | 4/2004 | Curro et al. |
| 6,726,870 B1 | 4/2004 | Benson et al. |
| 6,736,916 B2 | 5/2004 | Steinke et al. |
| 6,739,024 B1 | 5/2004 | Wagner |
| 6,787,000 B2 | 9/2004 | Burazin et al. |
| 6,794,626 B2 | 9/2004 | Kiermeier et al. |
| 6,808,791 B2 | 10/2004 | Curro et al. |
| 6,811,652 B2 | 11/2004 | Hollmark |
| 6,818,101 B2 | 11/2004 | Vinson et al. |
| 6,818,802 B2 | 11/2004 | Takai et al. |
| 6,830,800 B2 | 12/2004 | Curro et al. |
| 6,837,956 B2 | 1/2005 | Cowell et al. |
| 6,849,319 B2 | 2/2005 | Cree |
| 6,855,220 B2 | 2/2005 | Wildeman |
| 6,863,960 B2 | 3/2005 | Curro et al. |
| 6,872,274 B2 | 3/2005 | Kauschke et al. |
| 6,884,494 B1 | 4/2005 | Curro et al. |
| 6,916,438 B2 | 7/2005 | Berry |
| 6,916,969 B1 | 7/2005 | Helmfridsson et al. |
| 6,989,075 B1 | 1/2006 | Kao |
| 6,991,706 B2 | 1/2006 | Lindsay et al. |
| 7,005,558 B1 | 2/2006 | Johansson et al. |
| 7,037,569 B2 | 5/2006 | Curro et al. |
| 7,112,257 B2 | 9/2006 | Baggot |
| 7,147,453 B2 | 12/2006 | Boegli |
| 7,175,412 B2 | 2/2007 | Lin |
| 7,229,681 B2 | 6/2007 | Boegli |
| 7,232,613 B2 | 6/2007 | Nakagawa |
| 7,323,072 B2 | 1/2008 | Engelhart |
| 7,399,378 B2 | 7/2008 | Edwards et al. |
| 7,410,683 B2 | 8/2008 | Curro et al. |
| 7,413,630 B2 | 8/2008 | Graff |
| 7,423,003 B2 | 9/2008 | Volpenhein |
| 7,459,180 B2 | 12/2008 | Hamdar |
| 7,497,926 B2 | 3/2009 | Hermans |
| 7,521,588 B2 | 4/2009 | Stone |
| 7,527,615 B2 | 5/2009 | Roe |
| 7,553,532 B2 | 6/2009 | Turner et al. |
| 7,632,979 B2 | 12/2009 | Fujii |
| 7,682,686 B2 | 3/2010 | Curro et al. |
| 7,683,686 B2 | 3/2010 | Wang et al. |
| 7,732,657 B2 | 6/2010 | Hammons et al. |
| 7,754,312 B2 | 7/2010 | Nakajima et al. |
| 7,758,947 B2 | 7/2010 | Maschino |
| 7,799,176 B2 | 9/2010 | Schulz |
| 7,811,665 B2 | 10/2010 | Manifold et al. |
| 7,820,874 B2 | 10/2010 | Manifold et al. |
| 7,901,758 B2 | 3/2011 | Rasmussen |
| 7,939,168 B2 | 5/2011 | Manifold et al. |
| 7,960,020 B2 | 6/2011 | Manifold et al. |
| 7,967,801 B2 | 6/2011 | Hammons et al. |
| 7,989,058 B2 | 8/2011 | Manifold et al. |
| 7,993,317 B2 | 8/2011 | Hammons et al. |
| 8,012,309 B2 | 9/2011 | Pare et al. |
| 8,021,591 B2 | 9/2011 | Curro |
| 8,025,966 B2 | 9/2011 | Manifold et al. |
| 8,058,501 B2 | 11/2011 | Hammons et al. |
| 8,152,957 B2 | 4/2012 | Edwards et al. |
| 8,158,043 B2 | 4/2012 | Gibson et al. |
| 8,231,377 B2 | 7/2012 | Wittner et al. |
| 8,241,543 B2 | 8/2012 | O'Donnell et al. |
| 8,679,391 B2 | 3/2014 | O'Donnell et al. |
| 8,748,692 B2 | 6/2014 | Suzuki |
| 8,847,002 B2 | 9/2014 | Goh |
| 8,981,178 B2 | 3/2015 | Ng et al. |
| 9,023,261 B2 | 5/2015 | Mullane |
| 9,308,133 B2 | 4/2016 | Mullane |
| 2001/0029141 A1 | 10/2001 | Mizutani |
| 2002/0016122 A1 | 2/2002 | Curro et al. |
| 2002/0039867 A1 | 4/2002 | Curro et al. |
| 2002/0055310 A1 | 5/2002 | Falk et al. |
| 2002/0103469 A1 | 8/2002 | Chen et al. |
| 2002/0105110 A1 | 8/2002 | Dobrin et al. |
| 2002/0107495 A1 | 8/2002 | Chen et al. |
| 2002/0119720 A1 | 8/2002 | Arora et al. |
| 2002/0132544 A1 | 9/2002 | Takagaki |
| 2003/0021951 A1 | 1/2003 | Desai et al. |
| 2003/0028165 A1 | 2/2003 | Curro et al. |
| 2003/0085213 A1 | 5/2003 | Burckhardt et al. |
| 2003/0121380 A1 | 7/2003 | Cowell |
| 2003/0125687 A1 | 7/2003 | Gubernick et al. |
| 2003/0191442 A1 | 10/2003 | Bewick-Sonntag et al. |
| 2003/0191443 A1 | 10/2003 | Taylor et al. |
| 2003/0204178 A1 | 10/2003 | Febo |
| 2004/0015145 A1 | 1/2004 | Miura et al. |
| 2004/0110442 A1 | 6/2004 | Rhim |
| 2004/0121686 A1 | 6/2004 | Wong et al. |
| 2004/0126531 A1 | 7/2004 | Harvey et al. |
| 2004/0127875 A1 | 7/2004 | Hammons et al. |
| 2004/0131820 A1 | 7/2004 | Turner et al. |
| 2004/0137200 A1 | 7/2004 | Chhabra et al. |
| 2004/0157036 A1 | 8/2004 | Provost et al. |
| 2004/0161586 A1 | 8/2004 | Cree |
| 2004/0229008 A1 | 11/2004 | Hoying |
| 2004/0242097 A1 | 12/2004 | Hasenoehrl |
| 2004/0265533 A1 | 12/2004 | Hoying et al. |
| 2004/0265534 A1 | 12/2004 | Curro et al. |
| 2005/0021753 A1 | 1/2005 | Coleman |
| 2005/0051290 A1 | 3/2005 | Beasley, Jr. et al. |
| 2005/0064136 A1 | 3/2005 | Turner |
| 2005/0096614 A1 | 5/2005 | Perez et al. |
| 2005/0123726 A1 | 6/2005 | Broering et al. |

(56) References Cited

U.S. PATENT DOCUMENTS

| | | |
|---|---|---|
| 2005/0153100 A1 | 7/2005 | Zoller |
| 2005/0173085 A1 | 8/2005 | Schulz |
| 2006/0063454 A1 | 3/2006 | Chung |
| 2006/0087053 A1 | 4/2006 | Odonnell |
| 2006/0151914 A1 | 7/2006 | Gerndt |
| 2006/0194027 A1 | 8/2006 | Pourdeyhimi |
| 2006/0206072 A1 | 9/2006 | Malakouti |
| 2006/0286343 A1 | 12/2006 | Curro |
| 2007/0001270 A1 | 1/2007 | Curro et al. |
| 2007/0029694 A1 | 2/2007 | Cree |
| 2007/0093157 A1 | 4/2007 | Shannon et al. |
| 2007/0131368 A1 | 6/2007 | Xia |
| 2008/0217809 A1 | 9/2008 | Zhao |
| 2008/0221538 A1 | 9/2008 | Zhao |
| 2008/0221539 A1 | 9/2008 | Zhao |
| 2008/0221541 A1 | 9/2008 | Lavash |
| 2008/0221542 A1 | 9/2008 | Zhao |
| 2008/0224351 A1 | 9/2008 | Curro |
| 2009/0026651 A1 | 1/2009 | Lee |
| 2009/0029106 A1 | 1/2009 | Mauler |
| 2009/0258191 A1 | 10/2009 | Peacock |
| 2010/0001434 A1 | 1/2010 | Atkin |
| 2010/0032867 A1 | 2/2010 | Schmidt |
| 2010/0036338 A1 | 2/2010 | Hammons |
| 2010/0036346 A1* | 2/2010 | Hammons ......... A61F 13/51305 604/378 |
| 2010/0201024 A1 | 8/2010 | Gibson |
| 2010/0318047 A1 | 12/2010 | Ducker |
| 2011/0088859 A1 | 4/2011 | Hultcrantz et al. |
| 2011/0160691 A1 | 6/2011 | Ng |
| 2011/0196330 A1 | 8/2011 | Hammons |
| 2011/0221094 A1 | 9/2011 | Gross et al. |
| 2012/0049404 A1 | 3/2012 | Gibson et al. |
| 2012/0059343 A1 | 3/2012 | Kume |
| 2012/0064280 A1 | 3/2012 | Hammons |
| 2012/0064298 A1 | 3/2012 | Orr |
| 2012/0273146 A1 | 11/2012 | Curro |
| 2012/0273148 A1 | 11/2012 | Orr |
| 2012/0273990 A1 | 11/2012 | O'Donnell et al. |
| 2012/0273997 A1 | 11/2012 | Stone |
| 2012/0276238 A1 | 11/2012 | Strube |
| 2012/0276239 A1 | 11/2012 | Coe |
| 2012/0276331 A1 | 11/2012 | Orr |
| 2012/0276337 A1 | 11/2012 | Curro |
| 2012/0276341 A1 | 11/2012 | Lake |
| 2012/0277393 A1 | 11/2012 | Curro |
| 2012/0277701 A1 | 11/2012 | Stone |
| 2012/0277704 A1 | 11/2012 | Marinelli |
| 2012/0277705 A1 | 11/2012 | Marinelli |
| 2012/0277706 A1 | 11/2012 | Marinelli |
| 2012/0277707 A1 | 11/2012 | Orr |
| 2012/0277708 A1 | 11/2012 | Marinelli |
| 2012/0277709 A1 | 11/2012 | Marinelli |
| 2012/0277710 A1 | 11/2012 | Marinelli |
| 2012/0282436 A1 | 11/2012 | Coe |
| 2013/0158497 A1 | 6/2013 | Yamaguchi |
| 2014/0120323 A1 | 5/2014 | Lake et al. |
| 2014/0239537 A1 | 8/2014 | Mullane |
| 2014/0296815 A1 | 10/2014 | Takken et al. |
| 2014/0324009 A1 | 10/2014 | Lee et al. |
| 2014/0336608 A1 | 11/2014 | Hao |
| 2015/0038933 A1 | 2/2015 | Day et al. |
| 2015/0167215 A1 | 6/2015 | Manninen |
| 2015/0173956 A1 | 6/2015 | Coe |
| 2015/0173970 A1 | 6/2015 | Gross et al. |
| 2015/0209189 A1 | 7/2015 | Mullane |
| 2015/0209999 A1 | 7/2015 | Stone et al. |
| 2015/0230993 A1 | 8/2015 | Curro et al. |
| 2015/0250662 A1 | 9/2015 | Isele |
| 2015/0282686 A1 | 10/2015 | Hayase |
| 2015/0284892 A1* | 10/2015 | Galie ......... A61F 13/5126 28/165 |
| 2015/0313766 A1 | 11/2015 | Miao et al. |
| 2016/0038351 A1* | 2/2016 | Cecchetto ......... B29C 51/082 428/134 |
| 2016/0039109 A1* | 2/2016 | Cecchetto ......... A61F 13/5126 83/870 |
| 2016/0235590 A1 | 8/2016 | Coe et al. |
| 2016/0235592 A1 | 8/2016 | Coe et al. |
| 2016/0318236 A1 | 11/2016 | Mullane |
| 2017/0258651 A1 | 9/2017 | Hammons |
| 2017/0297292 A1 | 10/2017 | Maschino |
| 2017/0312143 A1 | 11/2017 | Splendiani |
| 2017/0356108 A1 | 12/2017 | Maschino |
| 2017/0360621 A1 | 12/2017 | O'Donnell et al. |
| 2018/0098894 A1 | 4/2018 | Hammons |
| 2018/0221220 A1 | 8/2018 | Kuramochi |
| 2018/0222077 A1 | 8/2018 | Cecchetto et al. |
| 2018/0256414 A1 | 9/2018 | Maschino |
| 2018/0369028 A1 | 12/2018 | Cecchetto |

FOREIGN PATENT DOCUMENTS

| | | | |
|---|---|---|---|
| CN | 102112083 | A | 6/2011 |
| CN | 102673030 | A | 9/2012 |
| CN | 202491475 | U | 10/2012 |
| CN | 103417337 | A | 12/2013 |
| CN | 103417338 | B | 4/2016 |
| EP | 0598970 | B2 | 6/1994 |
| EP | 0509012 | B1 | 7/1995 |
| EP | 0494112 | B1 | 4/1998 |
| EP | 0955159 | A1 | 11/1999 |
| EP | 0963747 | A1 | 12/1999 |
| EP | 1004412 | A1 | 5/2000 |
| EP | 1290995 | A2 | 3/2003 |
| EP | 1216818 | A3 | 12/2003 |
| EP | 1440197 | B1 | 1/2005 |
| EP | 1450741 | B1 | 6/2007 |
| EP | 2034072 | B1 | 9/2013 |
| EP | 2519402 | B1 | 2/2016 |
| FR | 1302937 | A | 9/1962 |
| JP | 2741816 | B2 | 2/1992 |
| JP | H04187146 | A | 7/1992 |
| JP | A2002544019 | | 12/2002 |
| JP | 3886466 | B2 | 3/2003 |
| JP | 2003116909 | | 4/2003 |
| JP | 4540590 | B2 | 11/2005 |
| JP | 4627035 | B2 | 12/2005 |
| JP | 2006175689 | A | 7/2006 |
| JP | 3880502 | | 2/2007 |
| JP | 2008073396 | | 4/2008 |
| JP | 4338327 | | 10/2009 |
| JP | 4928181 | B2 | 2/2012 |
| JP | 2015104650 | A | 6/2015 |
| JP | 2017038925 | A | 2/2017 |
| RU | 57593 | | 10/2006 |
| WO | WO9215445 | A1 | 9/1992 |
| WO | WO9515138 | A1 | 6/1995 |
| WO | WO0059438 | A1 | 10/2000 |
| WO | WO2002/100632 | A1 | 12/2002 |
| WO | WO2003/015681 | A1 | 2/2003 |
| WO | WO2004058121 | A1 | 7/2004 |
| WO | WO2004108037 | | 12/2004 |
| WO | WO2005011936 | A1 | 2/2005 |
| WO | WO2007001270 | A1 | 1/2007 |
| WO | WO2007069964 | A1 | 6/2007 |
| WO | WO2007069965 | A1 | 6/2007 |
| WO | WO2007069966 | A1 | 6/2007 |
| WO | WO2008107846 | A1 | 9/2008 |
| WO | WO2009005006 | A1 | 1/2009 |
| WO | WO2009010092 | A1 | 1/2009 |
| WO | WO2009013659 | A1 | 1/2009 |
| WO | WO2010135503 | A1 | 11/2010 |
| WO | WO2012156833 | A2 | 11/2012 |
| WO | WO2013047865 | A1 | 4/2013 |
| WO | 201598373 | | 7/2015 |
| WO | WO2015143772 | | 10/2015 |
| WO | WO2016019518 | A1 | 2/2016 |
| WO | WO2017171775 | A1 | 10/2017 |

(56) References Cited

FOREIGN PATENT DOCUMENTS

| WO | WO2017192592 A1 | 11/2017 |
| WO | WO2017214522 A1 | 12/2017 |

OTHER PUBLICATIONS

AA1002 International Search Report and written opinion for PCT/US2016/017310 dated Jun. 22, 2016.

AA964Q PCT Search Report and Written Opinion (PCT/CN2014/083774) dated Apr. 29, 2015.

\* cited by examiner

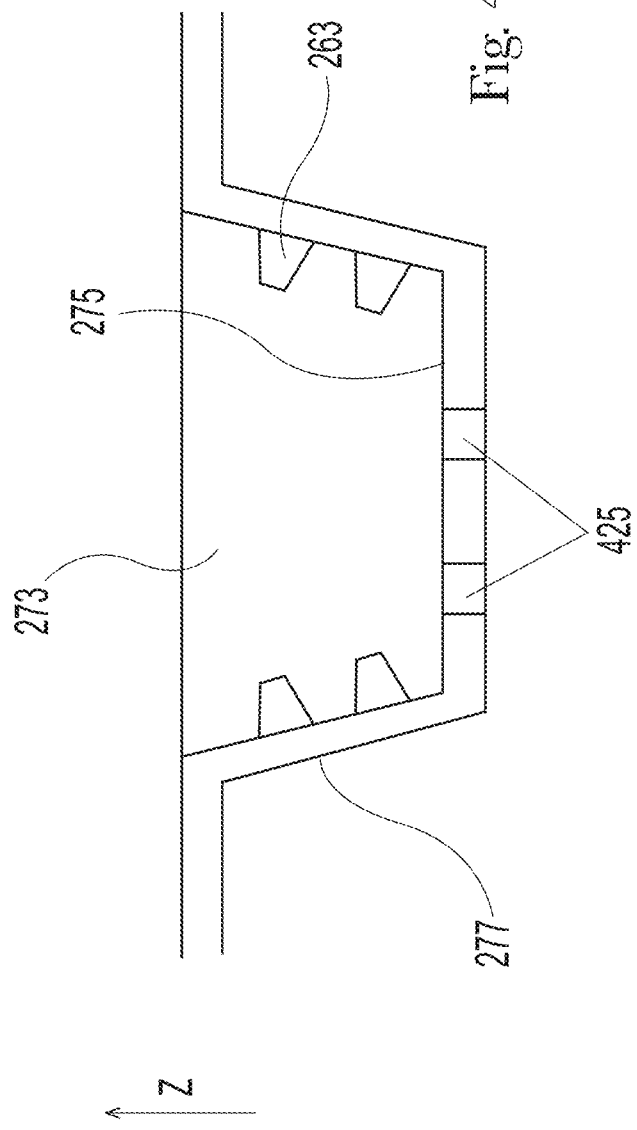

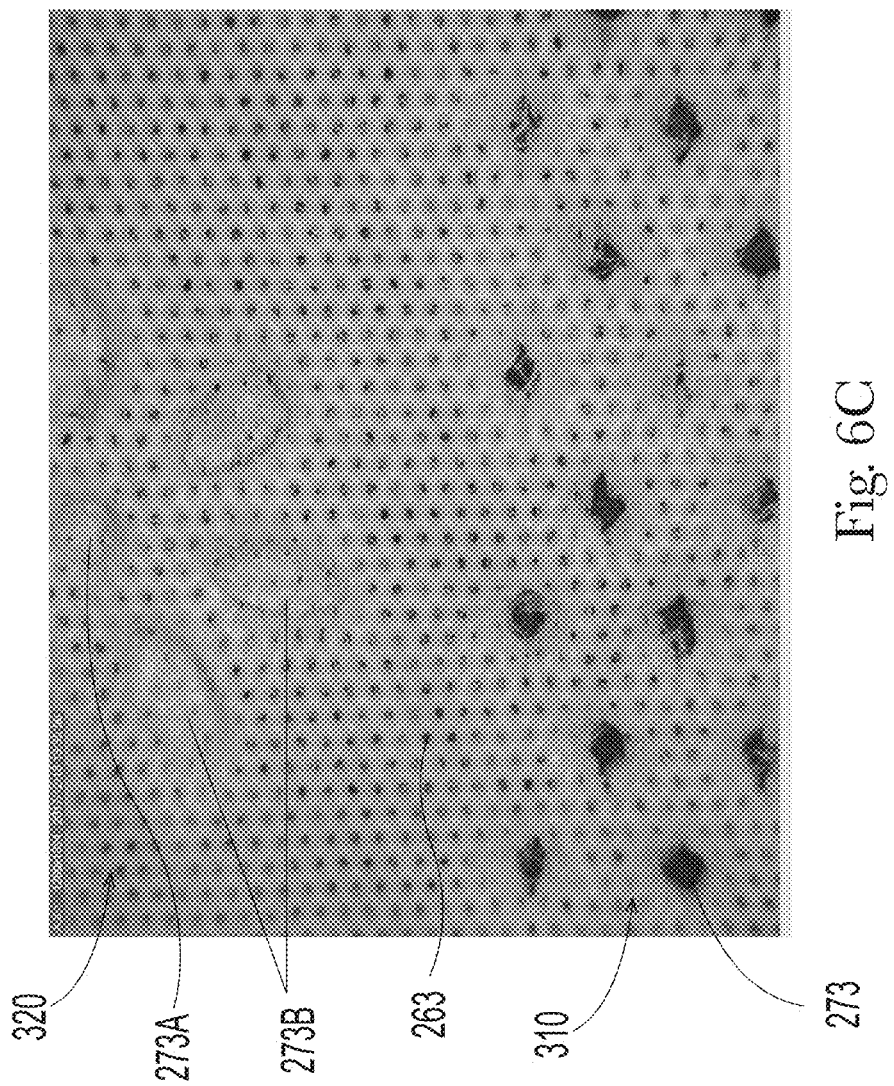

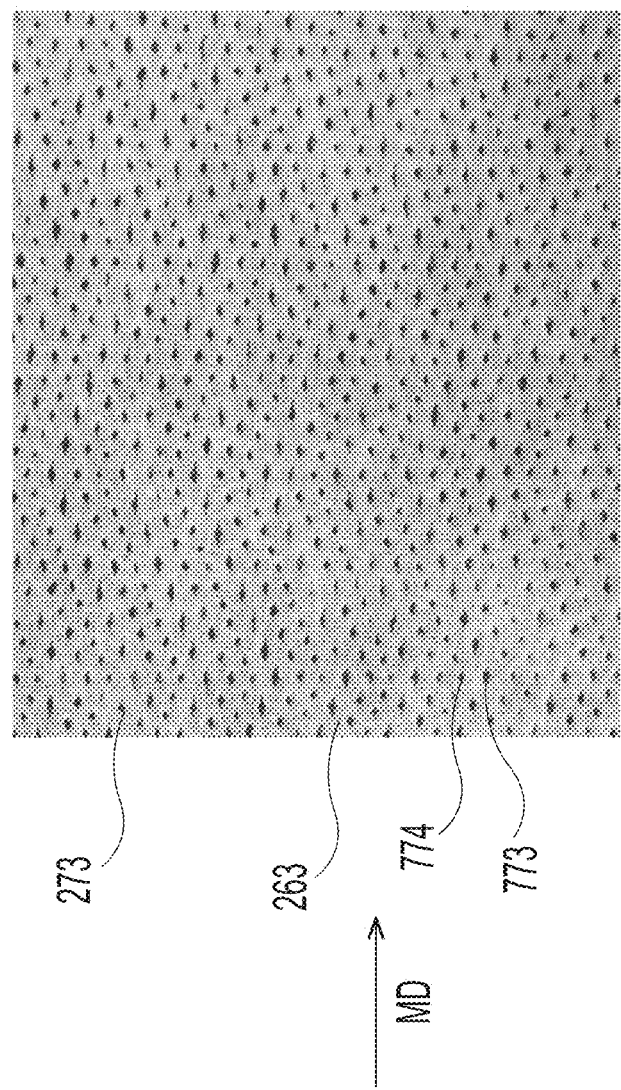

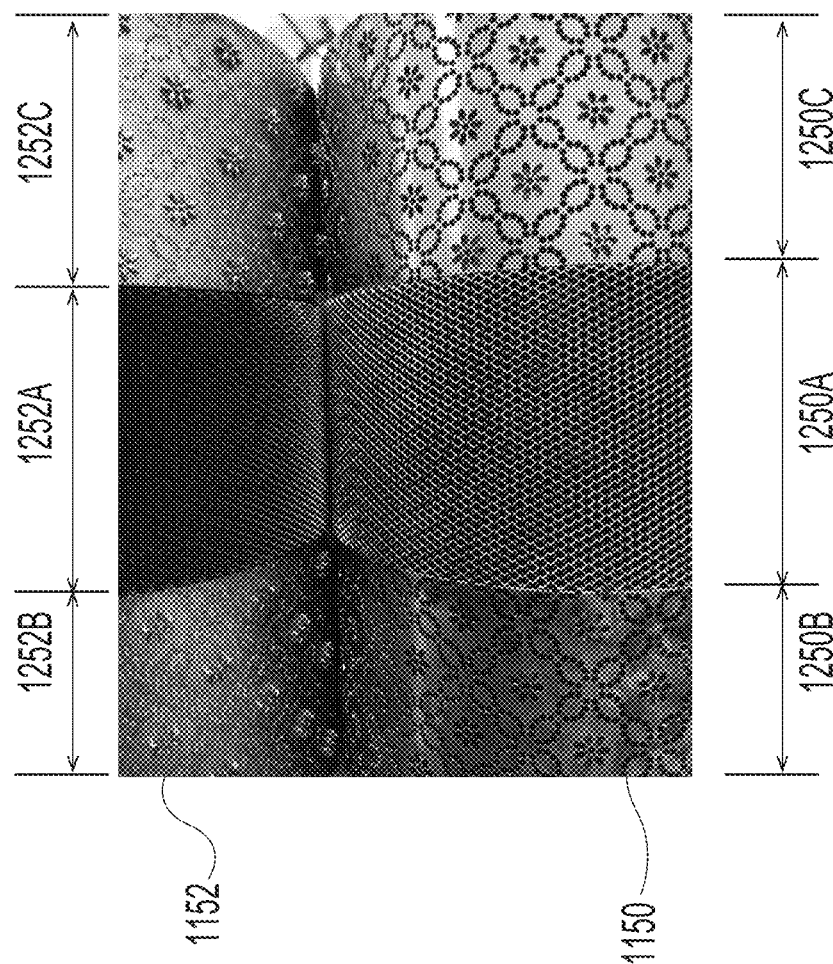

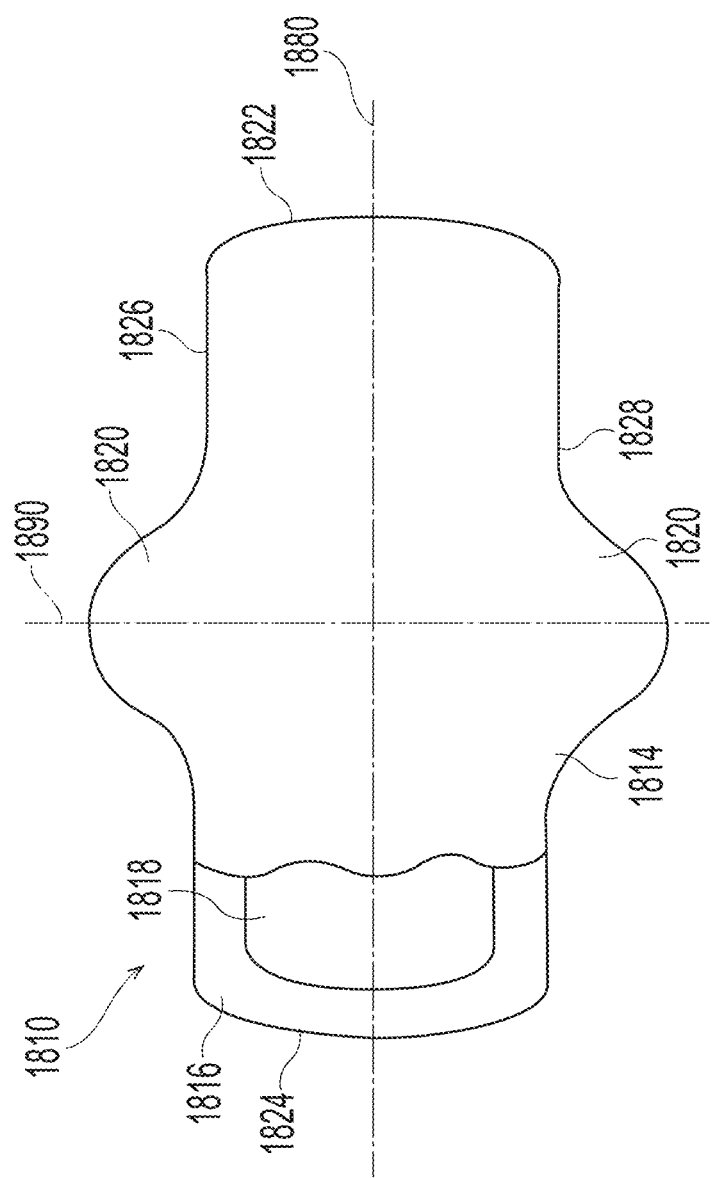

DISPOSABLE ABSORBENT ARTICLE

FIELD OF THE INVENTION

The present invention pertains to a disposable absorbent articles and methods of making the same.

BACKGROUND OF THE INVENTION

Disposable absorbent articles are widely used by a variety of consumers. In general, disposable absorbent articles comprise a topsheet, a backsheet, and an absorbent core disposed between the topsheet and the backsheet.

While there have been many developments over the years which improve the feel of the article or the performance of the article with regard to liquid acquisition and/or rewet, there has been some difficulty in trying to balance feel and liquid performance. For example, topsheets comprising nonwoven materials have been disclosed. Such topsheets can provide the user with a soft/comfortable feel; however, nonwoven topsheets may also lend themselves to higher rewet and may also have lower stain masking potential.

Material counterparts to nonwovens can include films. While film topsheets can alleviate some of the problems associated with nonwoven topsheets, film topsheets can have their own host of issues. For example, some consumers can discern a plastic-like feel for those articles which utilize a film topsheet. The plastic-feel, at least to some consumers, can be uncomfortable.

There have been advancements for nonwovens and films which are meant to be utilized as topsheets of absorbent articles. However, these advancements typically come with an increase in cost. The significant increase in cost can deter implementation of these new technologies.

Based on the foregoing, there is a need for a material which can overcome at least some of the deficiencies identified with regard to nonwoven or film topsheets.

SUMMARY OF THE INVENTION

The webs disclosed herein can provide a much better feel to the wearer over their film counterparts. Additionally, the webs described herein can provide good liquid acquisition speed as well as limit rewet.

An exemplary absorbent article of the present disclosure comprises a longitudinal centerline and a transverse centerline which is generally perpendicular to the longitudinal centerline, the absorbent article further comprising: a topsheet; a backsheet; an absorbent system disposed between the topsheet and the backsheet; and a material web comprising a film layer and a nonwoven layer, the material web comprising a plurality of micro-deformations and a plurality of macro-deformations, each of the macro-deformations comprising a distal end, wherein a first portion of macro-deformations comprises an open or partially open distal ends and wherein a second portion of macro-deformations comprises distal ends which are configured differently than the distal ends of the first portion, and wherein the material web forms a portion of the topsheet.

An exemplary method of making a material web in accordance with the present disclosure, comprises the steps of: obtaining a film; obtaining a nonwoven; laminating the film and the nonwoven to create a laminate web; forming a plurality of micro-deformations in at least one of the layers of the laminate web; and creating a first zone of macro-deformations having a first configuration and creating a second zone of macro-deformations having a second configuration that is different than the first configuration.

BRIEF DESCRIPTION OF THE DRAWINGS

FIG. 4 is a schematic representation showing a macro-deformation in accordance with the present disclosure.

FIGS. 6A-6C are photographs showing close up views of exemplary webs constructed in accordance with the present disclosure.

FIGS. 7A-7C are photographs showing close up views of exemplary webs constructed in accordance with the present disclosure.

FIG. 12 is a photograph showing a close up view of surface of a male/female roll arrangement with zones thereon.

FIG. 13 is a schematic representation of a feminine sanitary pad constructed in accordance with the present disclosure.

DETAILED DESCRIPTION OF THE INVENTION

Figure 1A:
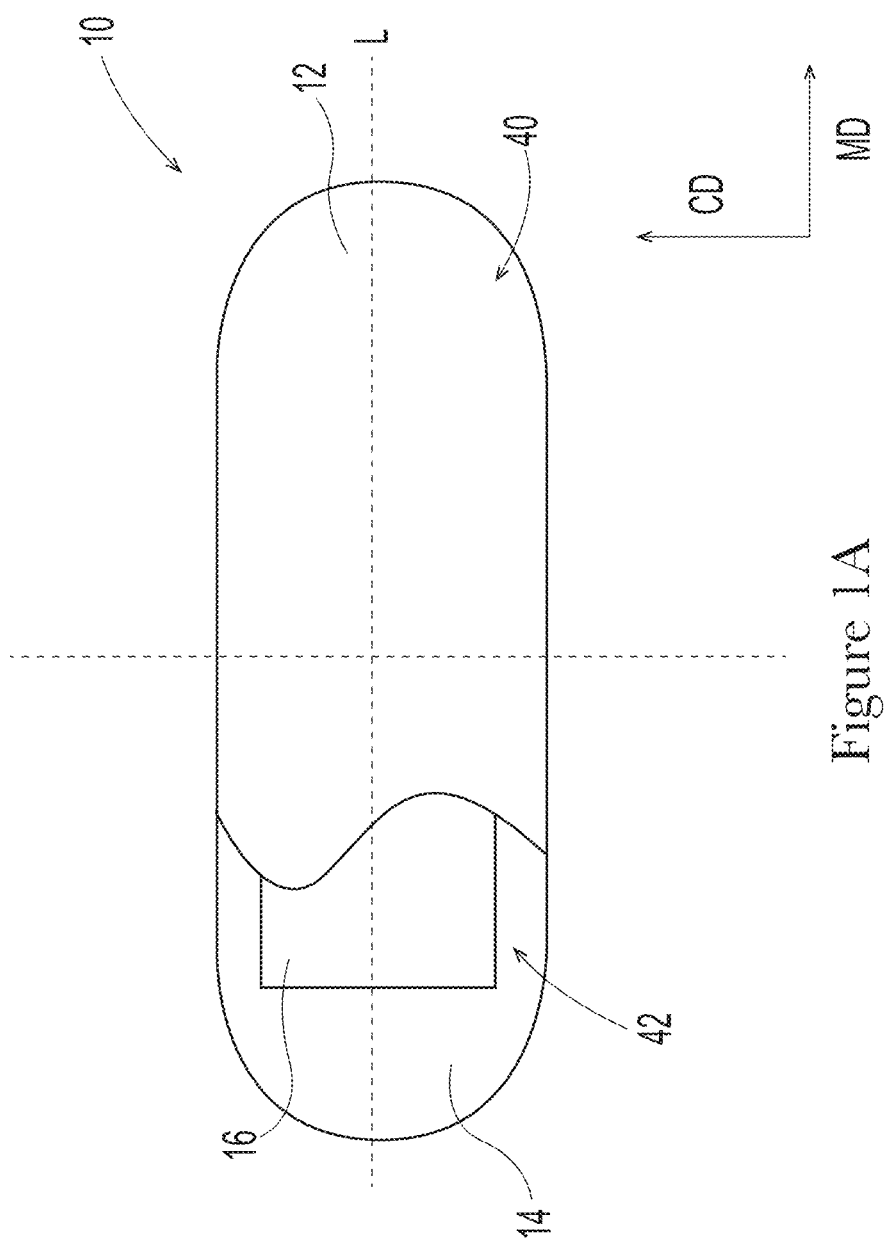
FIG. 1A is a schematic representation of a feminine sanitary pad.

The disposable absorbent articles of the present disclosure allow for good liquid performance with the flexibility of providing lower cost alternatives for materials. For example, topsheets described herein can provide the user with a soft, cushiony feel, while effectively controlling rewet potential. The following terms will provide some additional context for the description of the articles of the preset disclosure.

The term "absorbent article" includes disposable articles such as sanitary napkins, panty liners, tampons, interlabial devices, wound dressings, diapers, adult incontinence articles, wipes, and the like. At least some of such absorbent articles are intended for the absorption of body liquids, such as menses or blood, vaginal discharges, urine, and feces. Wipes may be used to absorb body liquids, or may be used for other purposes, such as for cleaning surfaces. Various absorbent articles described above will typically comprise a liquid pervious topsheet, a liquid impervious backsheet joined to the topsheet, and an absorbent core between the topsheet and backsheet. The nonwoven material described herein can comprise at least part of other articles such as scouring pads, wet or dry-mop pads (such as SWIFFER® pads), and the like.

As used herein "hydrophilic" and "hydrophobic" have meanings as well established in the art with respect to the contact angle of water on the surface of a material. Thus, a material having a water contact angle of greater than about 90 degrees is considered hydrophobic, and a material having a water contact angle of less than about 90 degrees is considered hydrophilic. Compositions which are hydrophobic, will increase the contact angle of water on the surface of a material while compositions which are hydrophilic will decrease the contact angle of water on the surface of a material. Notwithstanding the foregoing, reference to relative hydrophobicity or hydrophilicity between a material and a composition, between two materials, and/or between two compositions, does not imply that the materials or compositions are hydrophobic or hydrophilic. For example, a composition may be more hydrophobic than a material. In such a case neither the composition nor the material may be hydrophobic; however, the contact angle exhibited by the composition is greater than that of the material. As another example, a composition may be more hydrophilic than a material. In such a case, neither the composition nor the material may be hydrophilic; however, the contact angle exhibited by the composition may be less than that exhibited by the material.

The term "macro-deformation", as used herein, refers to structural features or elements that are readily visible and distinctly discernable to a human having 20/20 vision when the perpendicular distance between the viewer's eye and the web is about 12 inches (30 cm). Conversely, the term "micro-deformation" refers to such features that are not readily visible and distinctly discernable under such conditions. For the sake of clarity, macro-deformations specifically exclude embossments. Additional description regarding the difference between macro-deformations and embossments is provided herein.

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, meltblowing processes, spunbonding processes, hydroentangling, airlaying, and bonded carded web processes, including carded thermal bonding and air-through bonding. The basis weight of nonwoven fabrics is usually expressed in grams per square meter (gsm). The basis weight of the laminate web is the combined basis weight of the constituent layers and any other added components. Fiber diameters are usually expressed in microns (μm); fiber size can also be expressed in denier, which is a unit of weight per length of fiber. The basis weight of laminate webs suitable for use in the articles of the present disclosure can range from 8 gsm to 75 gsm, depending on the ultimate use of the material webs. For example, where the material webs disclosed herein are utilized as topsheets, the basis weight of the material web may be from 8 gsm to about 50 gsm, 14 gsm to 45 gsm, or between 20 gsm and about 40 gsm.

As used herein, the term a "polymeric film" comprise thermoplastic polymers having characteristic rheological properties which depend on their composition and temperature. Below their glass transition temperature, such thermoplastic polymers can be hard, stiff, and/or brittle. Below the glass transition temperature, the molecules are in rigid, fixed positions. Above the glass transition temperature but below the melt temperature range, thermoplastic polymers exhibit viscoelasticity. In this temperature range, the thermoplastic material generally has a certain degree of crystallinity and is generally flexible and to some degree deformable under a force. The deformability of such a thermoplastic is dependent on the rate of deformation, amount (dimensional quantity) of deformation, length of time it is deformed, and its temperature. Processes can be utilized to form materials comprising thermoplastic polymers, especially thermoplastic film, which are within this viscoelastic temperature range. Polymeric film can comprise a certain amount of ductility. Ductility, as used herein, is the amount of permanent, unrecoverable, plastic strain which occurs when a material is deformed, prior to failure (rupture, breakage, or separation) of the material. Materials that can be used as described herein can have a minimum ductility of at least about 10%, or at least about 50%, or at least about 100%, or at least about 200%. Polymeric film webs can include materials normally extruded or cast as films such as polyolefins, nylons, polyesters, and the like. Such films can be thermoplastic materials such as polyethylene, low density polyethylene, linear-low-density polyethylene, high density polyethylene, polypropylenes and copolymers, and blends containing substantial fractions of these materials. Such films can be treated with surface modifying agents to impart hydrophilic or hydrophobic properties, such as imparting a lotus effect. The polymer utilized in the polymeric film described herein may utilize polyolefin materials as described herein. As noted hereafter, polymeric film can be textured or otherwise altered from a strictly flat, planar configuration.

As shown in FIG. 1A, absorbent articles 10 of the present disclosure comprise a topsheet 12, a backsheet 14, and an absorbent system 16 disposed between the topsheet 12 and the backsheet 14. The absorbent article 10 further comprises a wearer-facing surface 40 and an opposing garment-facing surface 42. As shown, in some forms, the topsheet 12 forms at least a portion of the wearer-facing surface 40 and the backsheet 14 forms at least a portion of the garment-facing surface 42. For the sake of clarity, the absorbent system 16 may comprise an absorbent core as described herein and/or may comprise acquisition layer(s); distribution layer(s); secondary topsheet(s); an liquid management structure (LMS) as described herein.

Figure 1B:
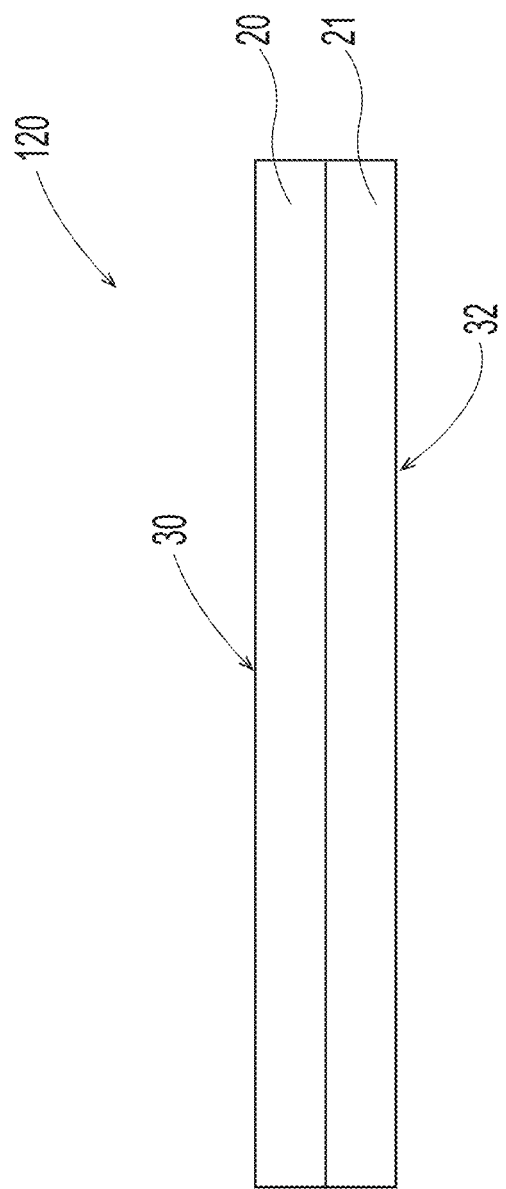
FIG. 1B is a schematic representation of a topsheet of the present disclosure.

Regarding FIG. 1B, the topsheet 12 may comprise a composite material web or a laminate material web, referred to hereafter as "material web." As shown, the material web 120 comprises a first layer 20 and a second layer 21. At least one of the first layer 20 or the second layer 21 is a nonwoven material, and at least one of the first layer 20 or the second layer 21 is a film material. The material web 120 comprises a first surface 30 and an opposing second surface 32. The first surface 30, in some forms, may correspond with the wearer-facing surface 40 in FIG. 1A. The second surface 32, in some forms, may correspond with the wearer-facing surface 40 in FIG. 1A.

The first layer 20 and the second layer 21 can be unrolled from their respective separate rolls of material and can be subsequently laminated to one another. The first layer 20 and the second layer 21 may be joined together via glue, heat, extrusion laminated with semi molten polymer, etc. to form the laminate. Where the first layer 20 and the second layer 21 are laminated together, the laminate material can be deformed contemporaneously such that deformations are present in both layers. Alternatively, the individual layers of the laminate material may be processed separately such that deformations present in the first layer are not present in the second layer or vice versa. Or, the deformations may be present in the first layer are not registered with the deformations in the second layer.

In contrast, where the material web is a composite material, the composite material comprises an integrally formed structure. For example, where the layers of the material web comprise a film and a nonwoven, one or more film layers can be formed on a nonwoven carrier web, e.g. via extrusion, coating, etc. The nonwoven carrier web may pass under an extrusion die at a speed that is coordinated with the extruder speed to form a very thin web. The faster the speed of the nonwoven carrier web, the thinner the resultant film layer. The nonwoven carrier may have a velocity which is equal to that of the screen upon which the laminate will be apertured.

From the extruder, polymeric material which makes up the film layer is extruded onto the nonwoven carrier web. It is believed that the softened state of the polymeric material allows the polymeric material to flow, at least to some extent, into interstices between the fibers of the nonwoven carrier web. This can allow for intimate contact between the film and the nonwoven carrier web and can eliminate the need for adhesive bonding or other joining methods between the nonwoven carrier web and the polymeric material. And, as noted previously, it is worth noting that the temperature of the polymeric material, when extruded onto the nonwoven carrier, is lower than its melting, i.e. molten, temperature. If the temperature of the polymeric material is too high, the polymeric material may flow into too deeply into the carrier web. Additionally, where the temperature of the polymeric material is too high, processing issues may occur with material sticking to the processing equipment. So, it is imperative that the polymeric material be provided with a sufficient length of time to cool off, at least to some extent, from its melting temperature.

In addition to the foregoing description of laminates and composites, the material web may comprise additional layers beyond the first and second layer described above.

Figure 2A:
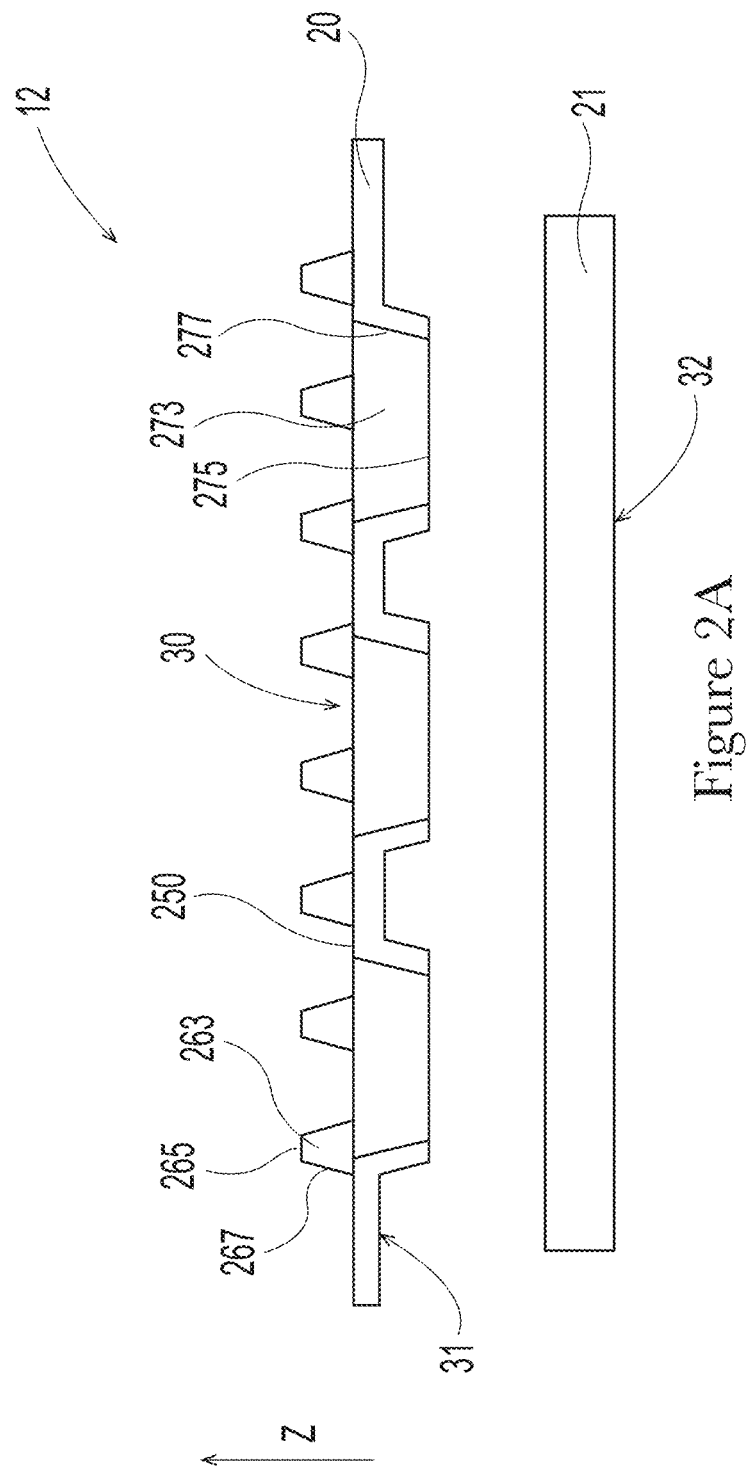
FIG. 2A is an exploded view of a representation of a topsheet of the present disclosure.

The combination of a nonwoven layer and film layer can provide the user of the absorbent article with a soft, cushiony-feeling topsheet. Additionally, because the composite or laminate material web comprises at least one film layer, the basis weight of the nonwoven can be decreased over what would be required if simply a nonwoven topsheet was being utilized. The additional basis weight of the nonwoven would likely be costlier to manufacture than the composite/laminate of the present disclosure. Similarly, it is believed that due to the combined basis weight of the composite or laminate material web, the basis weight of the film can be reduced as compared to only a film topsheet being utilized. The lower basis weight of film can provide for a more cushiony-soft feel to the wearer of the article.

Where the material web is utilized as a topsheet 12, the material web should acquire liquid insults effectively. To ensure that the material web acquires liquids in an efficient manner, a variety of structures may be provided to at least one or more layers of the material web. As shown in FIG. 2A, the first layer 20 may be provided with a plurality of micro-deformations 263 and a plurality of macro-deformations 273, each of which are considered out-of-plane with respect to the first surface 30. Specifically, each of the micro-deformations 263 and macro-deformations 273 respective distal ends are disposed away from the first surface 30 either in a positive or negative Z-direction. As shown, the micro-deformations may extend in a positive Z-direction away from the first surface 30. Each of the micro-deformations 263 comprises a distal end 265 and sidewalls 267 connecting the distal end 265 and the first surface 30. The distal end 265 may be closed, or the distal end 265 may be open or partially open.

Additionally, at least one or more layers of the material web may be provided with a plurality of macro-deformation 273 and land areas 250 between adjacent macro-deformations 273. Still referring to FIG. 2A, the first layer 20 may be provided with a plurality of macro-deformations 273 which extend in a negative Z-direction away from the first surface 30. Each of the macro-deformations 273 comprises a distal end 275 and sidewalls 277 connecting the distal end 275 and the first surface 30. As shown, the distal end 275 may be disposed subjacent to a second surface 31 of the first layer 20. However, the sidewalls 277 may be configured to extend between the first surface 30 and the second surface 31 of the first layer 20.

The distal ends 275 may be closed, the distal ends 275 may be open, or the distal ends 275 may be partially open, or combinations thereof. The macro-deformations 273 may be apertures through one or more layers of the material web.

The micro-deformations 263 may be oriented in the negative Z-direction such that the sidewalls 267 and distal end 265 are disposed subjacent the first surface 30. In contrast, the macro-deformations 273 may extend in the positive Z-direction such that the sidewalls 277 are disposed superjacent to the first surface 30. Or, the macro-deformations 273 may extend in the negative Z-direction as well as the micro-deformations 263, such that the macro-deformation distal ends 275 are disposed subjacent to the first surface 30. The macro-deformations 273 may be provided in zones such that macro-deformations 273 in a first zone extend in a positive Z-direction and macro-deformations in a second zone extend in the negative Z-direction. Similarly, the micro-deformations 263 may be provided in zones such that micro-deformations in a first zone extend in the positive Z-direction and micro-deformations in a second zone in the negative Z-direction.

Where the layers of the composite material web or laminate material web are processed contemporaneously, the micro-deformations 263 and macro-deformations 273 can be formed in all layers and configured as described above. For example, where the micro-deformations and/or macro-deformations are formed in two or more layers, fibers of the nonwoven layer can extend through the distal end 265 of the micro-deformations 263 and/or through the distal ends 275 of the macro-deformations 273.

Figure 2B:
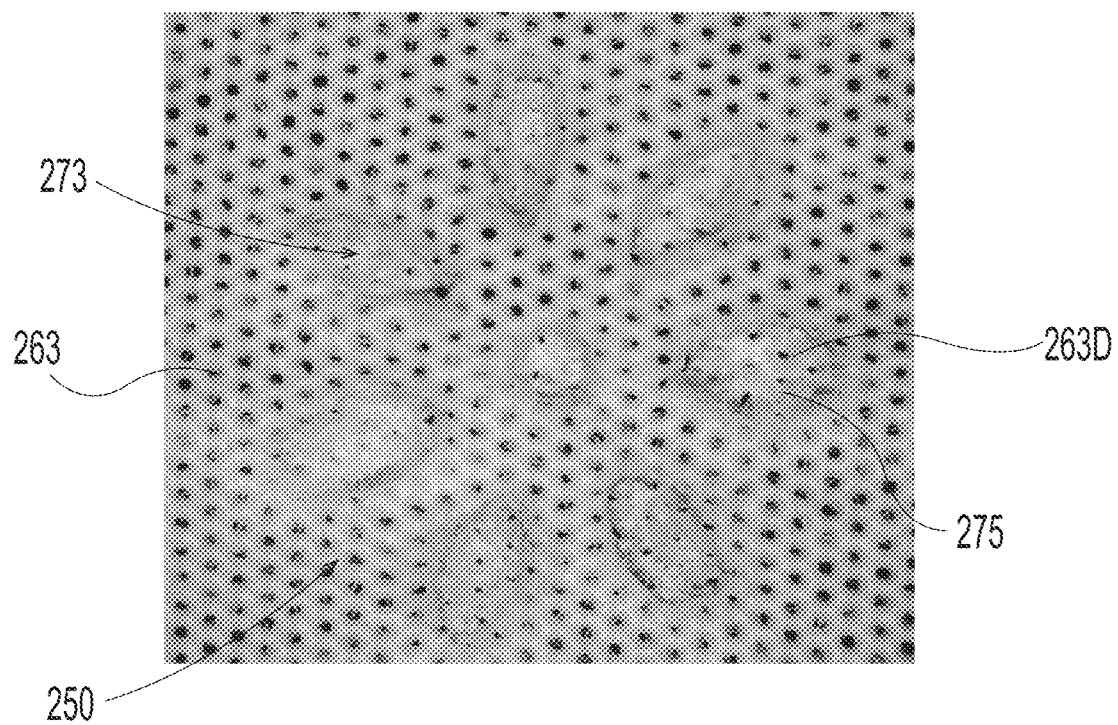
FIG. 2B is a photograph showing a close up view of an optional portion of a topsheet of the present disclosure.
Figure 2C:
FIG. 2C is a photograph showing a close up view of an exemplary portion of a topsheet of the present disclosure.

Exemplary micro-deformations 263 and macro-deformations 273 are shown in FIGS. 2B and 2C. As shown, the micro-deformations 263 may be partially open. For example, constituent material of one or more layers may bridge the distal end 265 (shown in FIG. 2A). FIG. 2B provides an example of a partially open distal end 275 of a macro-deformation 273. As shown, micro-deformations 263D within the macro-deformation distal ends may not expand during the formation of the macro-deformation 273. In order to provide adequate fluid acquisition properties additional macro-deformations 273 having open distal ends or at least partially open distal ends which are more open than the distal ends of the macro-deformations 273 shown in FIG. 2B may be provided.

The openness of the distal end 275 of FIG. 2B were measured per the "Distal End Aperture Area Measurement Method" disclosed herein. The data is provided below in Table 1. The diameter (from one distal end to an opposing distal end) was approximated to be about 7.7 mm.

TABLE 1

| Micro-deformation No. | Area (µm)² | Micro-deformation No. | |
|---|---|---|---|
| 1 | 2046.288 | 15 | 4092.575 |
| 2 | 1169.307 | 16 | 6820.959 |
| 3 | 1169.307 | 17 | 5846.536 |
| 4 | 1948.845 | 18 | 8185.151 |
| 5 | 4579.787 | 19 | 2533.499 |
| 6 | 3118.153 | 20 | 8574.92 |
| 7 | 3507.922 | 21 | 3118.153 |
| 8 | 2533.499 | 22 | 1948.845 |
| 9 | 1559.076 | 23 | 1169.307 |
| 10 | 3020.71 | 24 | 3118.153 |
| 11 | 3605.364 | 25 | 4092.575 |
| 12 | 2533.499 | 26 | 1559.076 |
| 13 | 3313.037 | 27 | 2533.499 |
| 14 | 6820.959 | 28 | 1559.076 |

The average open area of the micro-deformations 263D within the distal ends 275 of the macro-deformations 273 was about 3431 µm² with a standard deviation of about 2073. The minimum open area measured was 1169.307 µm² and the maximum open area was 8574.92 µm².

Figure 2D:
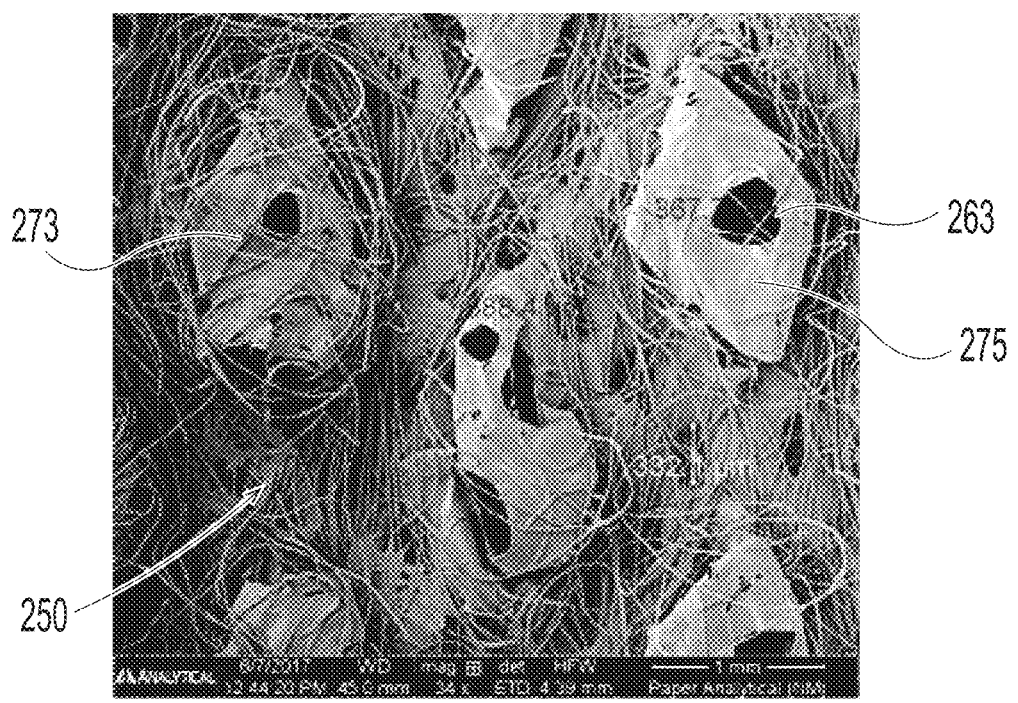
FIG. 2D is a photograph showing a close up view of an exemplary portion of a topsheet of the present disclosure.

As shown in FIGS. 2C and 2D, micro-deformations 263E on the distal ends 275 may expand such that they become larger than the micro-deformations 263 in land areas 250 between adjacent the macro-deformation 273. Where micro-deformations 263E are expanded on the distal ends 275 of macro-deformations 273, additional macro-deformations 273 with completely open distal ends, e.g. apertures, may not be required as the expanded/stretched micro-deformations 263E on the distal ends of the macro-deformations 273 may provide sufficient fluid acquisition properties.

Additionally, the nonwoven layer of the material web, as shown in FIGS. 2C and 2D may be provided in any suitable configuration. For example, as shown in FIG. 2C, the nonwoven material may be disposed on a second surface of the film layer such that nonwoven material is disposed, in part, on an inner surface of the side walls of the macro-deformations 273. As another example, as shown in FIG. 2D, the nonwoven material may be disposed on a first surface of the film layer such that the nonwoven material is disposed, in part, on an outer surface of the side walls of the macro-deformations 273. Regardless of the orientation of the nonwoven layer on the film layer, it may be beneficial for the filaments/fibers of the nonwoven to be present more along the sidewalls of the macro-deformation 273 as opposed to the distal end. It is believed that where more filaments are present at the distal ends of the macro-deformations 273, the filaments/fibers of the nonwoven may inhibit the acquisition/draining of fluid from the macro-deformation.

The openness of the distal ends 275 of FIG. 2C were measured per the "Distal End Aperture Area Measurement Method" disclosed herein. The data is provided below in Table 2.

TABLE 2

| Micro-deformation No. | Area (µm)² | Micro-deformation No. | |
|---|---|---|---|
| 1 | 30373.013 | 13 | 23472.345 |
| 2 | 36064.805 | 14 | 7983.62 |
| 3 | 12793.939 | 15 | 18284.252 |
| 4 | 7681.4 | 16 | 51679.455 |
| 5 | 58076.425 | 17 | 37298.866 |
| 6 | 51629.085 | 18 | 14682.808 |
| 7 | 42361.035 | 19 | 31808.553 |
| 8 | 56112.001 | 20 | 28458.959 |
| 9 | 19644.237 | 21 | 53543.139 |
| 10 | 19795.347 | 22 | 31153.746 |
| 11 | 56288.295 | 23 | 9167.311 |
| 12 | 76688.08 | | |

The average open area of the micro-deformations 263E within the distal ends 275 of the macro-deformations 273 was about 33697 µm² with a standard deviation of about 19197. The minimum open area measured was 7681.4 µm² and the maximum open area was 76688.08 µm².

In reviewing the data from Tables 1 and 2, for those areas of the absorbent article which are expected to acquire liquid insults, the average area of the micro-deformations 263E within the distal ends 275 should be greater than about 5,500 µm². For example, the average open area for micro-deformations 263E within a distal end 275 of the macro-deformations may be greater than about 10,000 µm², preferably greater than about 15,000 µm², more preferably greater than about 20,000 µm², or most preferably greater than about 25,000 µm², specifically reciting all values within these ranges and any ranges created thereby.

As noted hereafter, the macro-deformations 273, when fully open, may comprise an open area of up to 15 mm². However, where the distal ends 275 of the macro-deformations 273 are only partially open, a plurality of micro-deformations 263E are typically disposed on the distal ends 275. So, each of the micro-deformations 263E may have an average open area of up to about 7 mm², between about 10,000 µm² and about 7 mm², between about 15,000 µm² and about 5 mm², between about 20,000 µm² to about 4 mm², and from about 25,000 µm² to about 3 mm², specifically reciting all values within these ranges and any ranges created thereby.

The overall open area of the distal ends 275 of the macro-deformations 273 in the areas of expected fluid acquisition can be 100 percent as noted herein. However, all or a portion of the distal ends 275 of these macro-deformations 275 may be only partially open as disclosed herein. Where distal ends area constructed with only partially open distal ends, the open area may be less than about 90 percent, less than about 75 percent, less than about 60 percent, or less than about 50 percent, specifically including all values within these ranges and any ranges created thereby.

In contrast, for those areas of the absorbent article which are not expected to acquire liquid insults, but rather to provide aesthetically pleasing elements for the consumer, the average open area may be less than about 15,000 µm², less than about 8,000 µm², less than about 6,000 µm², or less than about 5,000 µm², specifically reciting all values within these ranges and any ranges created thereby. As depicted in FIG. 2B, there are only a few of the micro-deformations 263D within the macro-deformation 273 distal ends 275 that are completely occluded, i.e. no open area. So, while a laudable goal may be to achieve an average open area of zero µm², achieving such a goal may introduce much higher production costs due to increased manufacturing complexity. Accordingly, an acceptable lower limit on the average open area for these micro-deformations 263D is from about 1,000 µm² to about 3,000 µm². Such micro-deformations 263D may not be readily perceptible to the naked eye and therefore may preserve the aesthetic quality of the pleasing consumer element.

The overall open area of the distal ends 275 of the macro-deformations 273 in those areas that are not expected to contribute to fluid acquisition can be zero percent or greater. For example, the overall open area for these distal ends 275 can be greater than about 0.01 percent, greater than about 0.05 percent, greater than about 1 percent, greater than about 2 percent, or greater than about 5 percent, specifically reciting all values within these ranges and any ranges created thereby.

Additionally, for those areas of the absorbent article which are not expected to readily absorb fluid insults, embossments may be utilized. It is believed that any micro-deformations in a distal end of an embossment would be occluded to a greater extent than the micro-deformations 263D associated with the macro-deformations 273 of FIG. 2B. It is believed that the average open area of the micro-deformations in the distal end of an embossment would be less than about 5,000 µm², less than about 3,000 µm², or less than about 1,000 µm², specifically reciting all values within these ranges and any ranges created thereby.

Figure 2E:
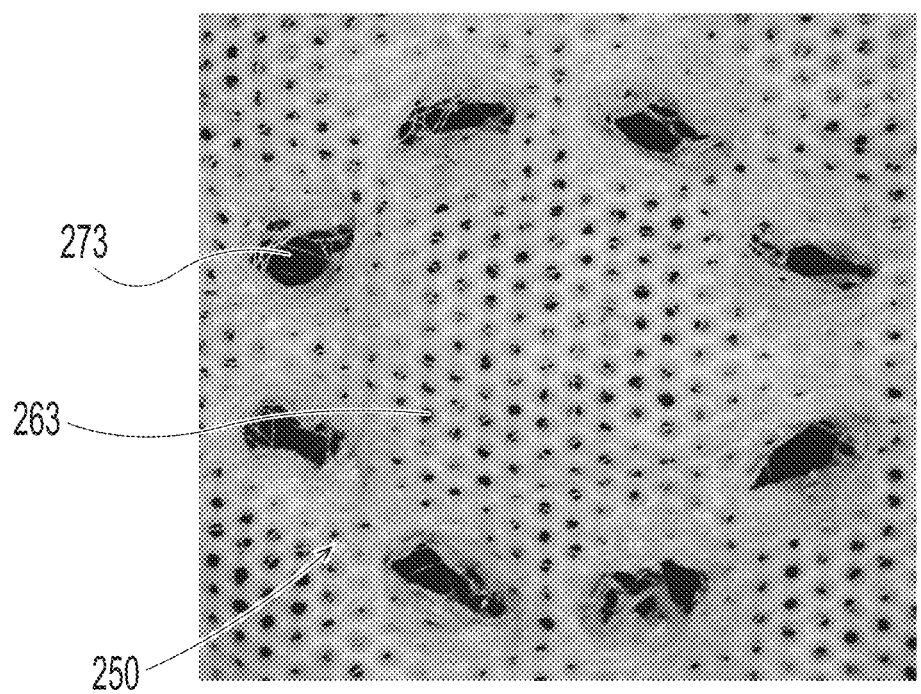
FIG. 2E is a photograph showing a close up view of an exemplary portion of a topsheet of the present disclosure.

Regarding FIG. 2E, partially open macro-deformations 273 and partially open micro-deformations 263 are shown. Composite or laminate material webs of the present disclosure may comprise a plurality of micro-deformations 263 that have open distal ends and a plurality of micro-deformations 263 that have partially open distal ends. In conjunction with these micro-deformations, another plurality of micro-deformations 263 may comprise closed distal ends. Similarly, as shown, the macro-deformations 273 may comprise constituent material which bridges their respective distal ends thereby creating a plurality of individual openings of varying sizes.

As noted previously, the micro-deformations 263 may have open proximal ends, open or closed distal ends, and sidewalls. The micro-deformations 263 may extend outwardly from a surface of the material web. The micro-deformations 263 provide microtexture to the material web. The micro-deformations 263 can, for example, be microapertures or micro bubbles, examples of which are disclosed in U.S. Pat. No. 7,454,732, issued to Stone et al. and U.S. Pat. No. 4,839,216 issued to Curro et al., U.S. Pat. No. 4,609,518 issued to Curro et al. Where the micro-deformations 263 are micro-apertures, the apertures can have an area of between about 0.01 mm² and about 0.78 mm².

The micro-deformations 263 can be discrete extended elements having a diameter shorter than a minor axis of macro-deformations 273 formed in the web. For example, the discrete extended elements have a diameter of less than about 500 microns; the discrete extended elements can have an aspect ratio of at least about 0.2; and/or the web comprises at least about 95 discrete extended elements per square centimeter. References disclosing such a plurality of discrete extended elements include WO 01/76842; WO 10/104996; WO 10/105122; WO 10/105124 and US20120277701A1. Macro-deformations 273 are discussed in additional detail hereafter.

For the macro-deformations, there are two types of aspect ratios which may be of import. An LW (length to width, both in cross section in an MD/CD plane) aspect ratio and a WH (width to height) aspect ratio. The LW aspect ratio can be from about 0.2 to about 1.5, from about 0.5 to about 1.25, or from about 0.7 to about 1.1, specifically reciting all values within these ranges and any ranges created thereby. The WH aspect ratio can be from about 0.1 to about 1.1, from about 0.4 to about 1, or from about 0.7 to about 0.9, specifically reciting all values within these ranges and any ranges created thereby.

Figure 3B:
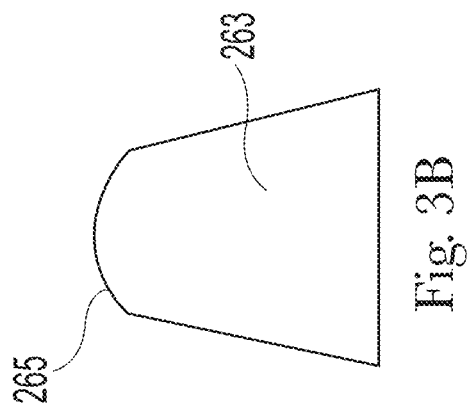
FIGS. 3A-3B are schematic representations showing a micro-deformation in accordance with the present disclosure.
Figure 3A:
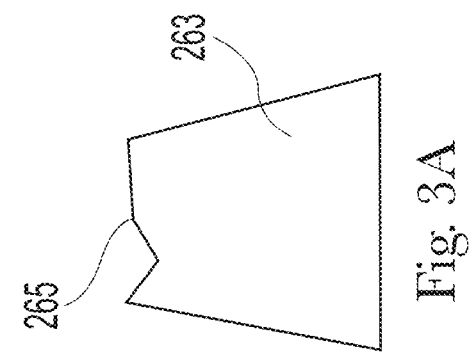

Still referring to FIGS. 3A and 3B, as noted previously, the micro-deformations 263 may comprise an open distal end 265 or a closed distal end 265. Schematic representations of the open and closed micro-deformation distal ends 265 are provided in FIGS. 3A and 3B, respectively. Additionally, as noted previously, in some forms, the distal ends 265 of the micro-deformations 263 may be partially open.

Referring now to FIGS. 2A and 4, as noted previously, the distal end 275 of the macro-deformations 273 may comprise a closed end or a partially open end. As shown, the macro-deformation 273 of FIG. 4 may comprise one or more openings/apertures 425 in the distal end 275. As discussed previously, the openings/apertures 425 may be due to expanded micro-deformations 263E in the distal end 275. Additionally, micro-deformations 263 may be disposed on the sidewalls 277 of the macro-deformation 273. During the formation of the macro-deformations 273, the constituent material of the composite or laminate can be stretched in a plurality of discrete areas each of which correspond to the macro-deformations 273. So, the micro-deformations 263 in the sidewalls 277 and/or the distal end 275 may be similarly stretched. This stretching can cause the micro-deformations 263 in the sidewalls 277 and/or distal end 275 to open up further than their non-stretched micro-deformation 263 counterparts. Macro-deformations 273 may be configured such that the micro-deformations 263 in the sidewalls 277 and/or distal ends 275 may be the same size as their micro-deformation 263 counterparts outside of the macro-deformations 273. Or macro-deformations 273 may be configured such that the micro-deformations 263 in the sidewalls 277 and/or distal ends 275 may be smaller (smaller open area) than their micro-deformation 263 counterparts which are outside of the macro-deformations 273.

As noted previously, the macro-deformations 273 or a portion thereof may be configured such that 100 percent of their respective distal ends 275 may be open. Alternatively, or in conjunction with the foregoing, macro-deformations 273 or a portion thereof may be configured such that their respective distal ends 275 are closed. Also, independent of the foregoing or in conjunction with any combination of the foregoing, the macro-deformations 273 or a portion thereof may be configured such that their distal ends 275 are between 5 percent to about 90 percent open, about 15 percent to about 75 percent open, or from about 25 percent to about 60 percent open.

Figure 5A:
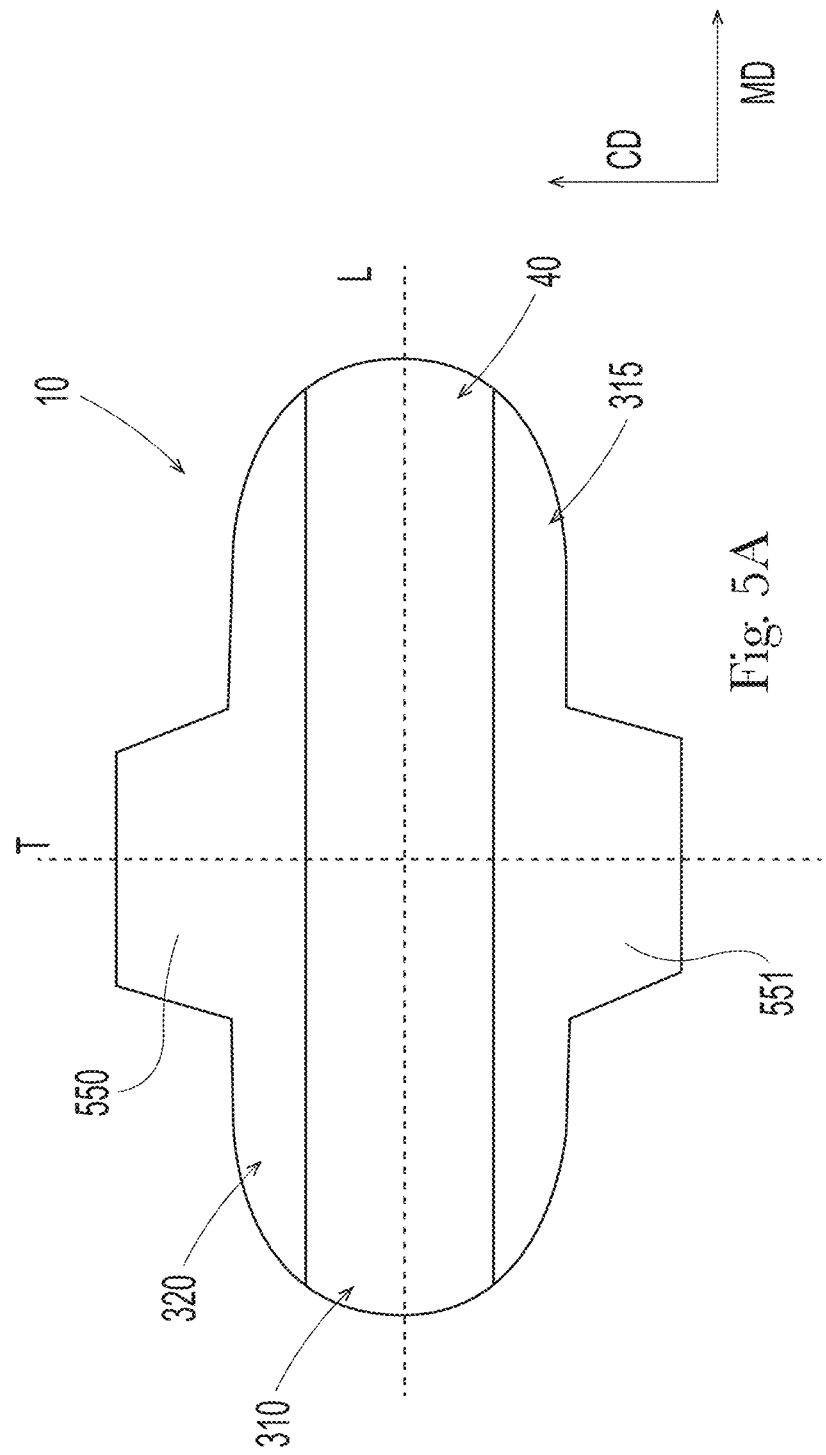
FIGS. 5A-5B are schematic representations of absorbent articles in accordance with the present disclosure highlighting some exemplary zone of the articles.

The micro-deformations and macro-deformations can be arranged on a disposable absorbent article in a myriad of ways. The inventors have found that some of the arrangements described herein can provide good fluid acquisition along with comfort and pleasing aesthetics to the wearer. One exemplary arrangement is shown in FIG. 5A. As shown, a first zone 310 may be arranged longitudinally (generally aligned with longitudinal axis L) with respect to the absorbent article 10. A second zone 315 and third zone 320 may flank the first zone 310. As shown, each of the first zone 310, second zone 315, and third zone 320 may extend the full length of the absorbent article 10. Additionally, the first zone 310 may additionally comprise a target area 575 (shown in FIG. 5B) which may correspond to the expected region of fluid entry into the absorbent article 10.

The first zone 310 may comprise between 20 percent to about 60 percent of the width of the absorbent article 10, where the width of the absorbent article is generally parallel to a transverse axis T. And, the first zone 310 may straddle the longitudinal axis L. The second zone 315 and third zone 320 may each comprise between 14 percent to about 40 percent of the width of the absorbent article 10. And where the absorbent article 10 comprises wings, the wings may be comprised by the second zone 315 and the third zone 320. Alternatively, the wings may be associated with different zones and may comprise different structures than those provided to the second and third zones.

Figure 5B:
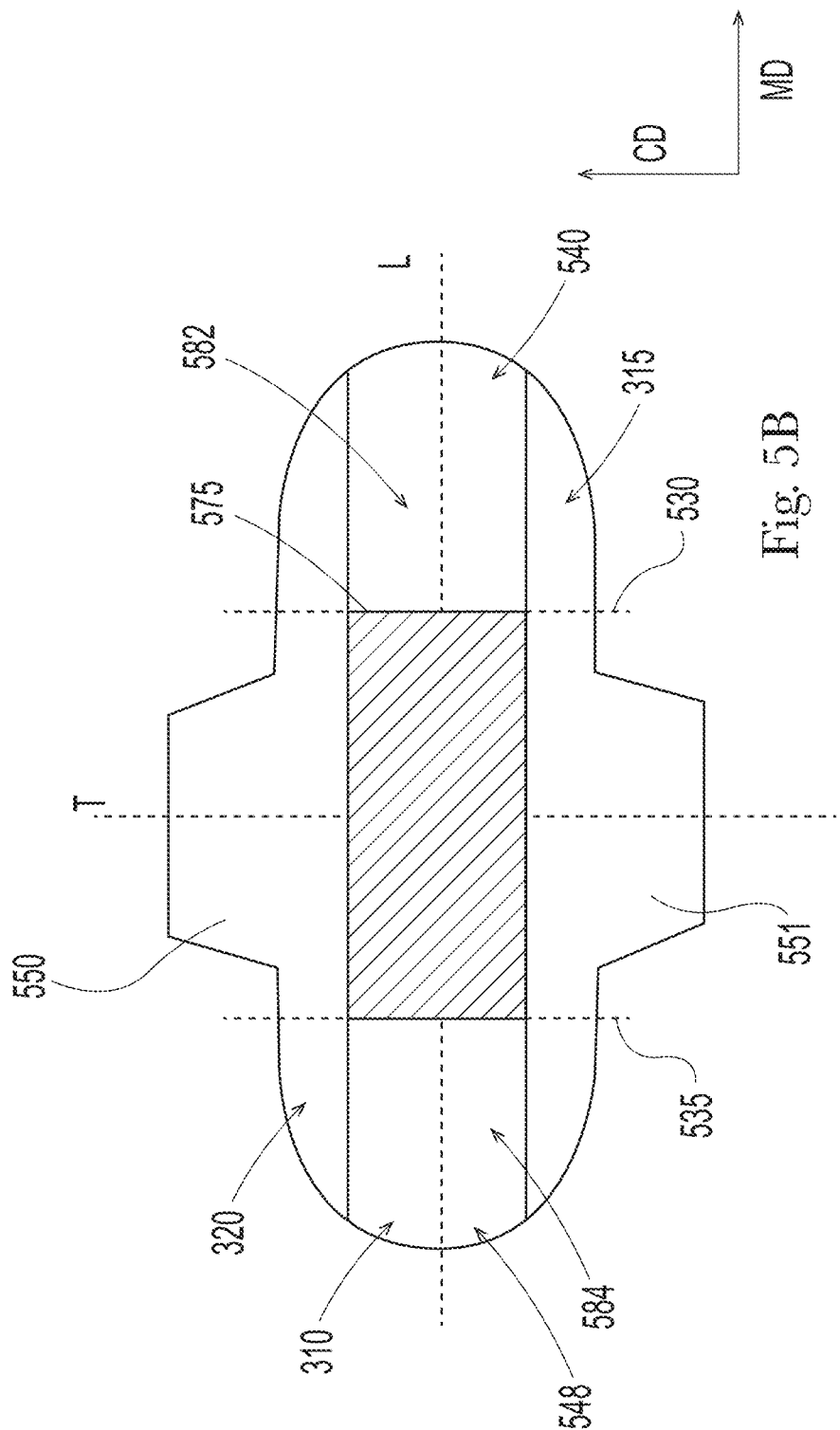

Referring now to FIGS. 5A and 5B, where the first zone 310 comprises the target area 575, the target area 575 generally corresponds to the region of intended fluid entry for the article 10. For menstrual pads, the intended region of fluid entry may be the location on the menstrual pad that corresponds to the vaginal opening. For adult incontinence articles, the intended region of fluid entry may be the location of the incontinence article that corresponds to the urethra or the vulva region as labial tissue can obscure the pathway from the urethra to the absorbent article. And, in general, the target area 575 may correspond to a portion of the absorbent article 10 that is positioned between the thighs of the wearer during use. The target area 575 may comprise the transverse axis T and/or the longitudinal axis L. For example, the target area 575 may be asymmetrically disposed about the transverse axis T, e.g. disposed on one side of the transverse axis T or disposed more on one side of the transverse axis T than the other side of the transverse axis T. A method for determining the extent of the target area 575 is disclosed hereafter. For ease of visualization, boundaries 530 and 535 for the target area 575 are shown.

The target area 575 may have any suitable length. For example, the target area 575 may extend a distance greater than or equal to about 15 percent of the total length of the article, greater than or equal to about 20 percent of the total length of the article, greater than or equal to about 30 percent of the total length of the article, greater than or equal to about 40 percent of the total length of the article, or greater than or equal to about 50 percent of the total length of the article, specifically including all values within these ranges and any ranges created thereby.

Where the target area 575 does not occupy the full length of the absorbent article 10, the first zone 310 may further comprise a first end area 582 and a second end area 584. The first end area 582 may be disposed longitudinally outboard of the boundary 530 in a first end region 540. Similarly, the second end area 584 may be disposed longitudinally outboard of the boundary 535 in a second end region 548. The first end region 540 and the second end region 548 may comprise the first zone 310, the second zone 315, and the third zone 320.

The first end region 540 and/or the second end region 548 may comprise about 45 percent of the total length of the absorbent article, about 30 percent of the length of the absorbent article, about 20 percent of the length of the absorbent article, about 15 percent of the length of the absorbent article, any combinations thereof, specifically including all values within these ranges and any ranges created thereby.

Referring now to FIGS. 1A, 2, 5A, and 5B, the target area 575 may comprise a plurality of micro-deformations 263 as described herein. The micro-deformations 263 may comprise open and/or closed distal ends 265 which extend in a positive Z-direction and form a portion of the wearer-facing surface 40 of the absorbent article 10. The target area 575 may further comprise a plurality of macro-deformations 273. Where the micro-deformations 263 are closed, at least a portion of the macro-deformations comprise distal ends 275 which are open to allow for adequate fluid acquisition. In addition, the target area 575 may comprise a combination of macro-deformations with closed distal ends 275 and macro-deformations 273 that are open at their distal ends 275, and/or macro-deformations with partially open distal ends.

Where the micro-deformations 263 comprise open distal ends 265, macro-deformations 273 may comprise open or partially open distal ends 275. For example, the macro-deformations 273 may be formed by stretching the first layer 20 or the second layer 21. During stretching the micro-deformations 263 within the macro-deformations 273 may be expanded. So, the open distal ends 265 of the micro-deformations 263 within the macro-deformations 273 are stretched and thereby create apertures 425 in the distal end 275. And, as noted previously, the micro-deformations 263 disposed on the sidewalls 277 of the macro-deformations 273 may similarly be stretched and form apertures in the sidewalls 277. In addition, the target area 575 may comprise a plurality of macro-deformations 263 with closed distal ends 275.

The second zone 315 and third zone 320 may comprise a plurality of micro-deformations 263. The micro-deformations 263 of the second zone 315 and the third zone 320 may comprise open distal ends 265 or closed distal ends 265. Or, the micro-deformations 263 may comprise a combination of open and closed distal ends 265. In addition, the second zone 315 and the third zone 320 may comprise a plurality of macro-deformations 273. In some forms, the macro-deformations 273 in the second zone 315 and/or third zone 320 may comprise closed distal ends 275. The macro-deformations 273 within the second zone 315 and the third zone 320 may be partially open. The macro-deformations 273 within the second zone 315 and third zone 320 may be open to a lesser extent than the macro-deformations 263 of the target area 575. Additionally, forms are contemplated where the macro-deformations 273 in the second zone 315 and third zone 320 are open to the same extent as the macro-deformations 273 in the target area 575. As shown, the second zone 315 and the third zone 320 may extend over wings 550 and 551.

Regardless of the degree of openness of the distal ends 275 of the macro-deformations 273 of the second zone 315 and third zone 320 may comprise a lower density of macro-deformations 273 (number of macro-deformations per square cm) than the target area 575. For example, the second zone 315 and the third zone 320 may comprise a plurality of macro-deformations 273 having a density of from between about 0 per square centimeter to about 15 per square centimeter. In contrast, the target area 575 may comprise a plurality of macro-deformations 273 having a density of from between about 5 per square centimeter to about 60 per square centimeter. The target area 575 may comprise macro-deformations 273 with a density of from about 5 to about 60, or from about 10 to about 50, or from about 20 to about 40 per/cm$^2$, specifically including all values within these ranges and any ranges created thereby.

Where the first zone 310 comprises different types of macro-deformations 273, the opposite may be true. For example, a first portion of macro-deformations 273 may comprise apertures, e.g. open distal ends 275, while a second portion of macro-deformations 273 may comprise partially open or closed distal ends 275. The first portion of macro-deformations 273 may have a density which is greater than that of the second portion. The first zone 310 may have a higher density of the second portion of macro-deformations 273 versus that of the first portion of macro-deformations 273.

The first zone 310, including the first end area 582 and the second end area 584 may be similarly configured to the target area 575. Or, the first zone 310, including the first end area 582 and the second end area 584 may be similarly configured to the second zone 315 and the third zone 320. One benefit of providing the first end area 582 and the second end area 584 with different structures than the target area 575 is with regard to stiffness. Where the macro-deformations in the first end area 582 and/or second end area 584 comprise apertures, the stiffness of the absorbent article in those areas may decrease. The decrease in stiffness in the first end area 582 and/or second end area 584 can increase the difficulty of product application to the underwear of the wearer. And, apertures in the first end area 582 and/or second end area 584 may create a negative perception amongst consumers.

Figure 6A:
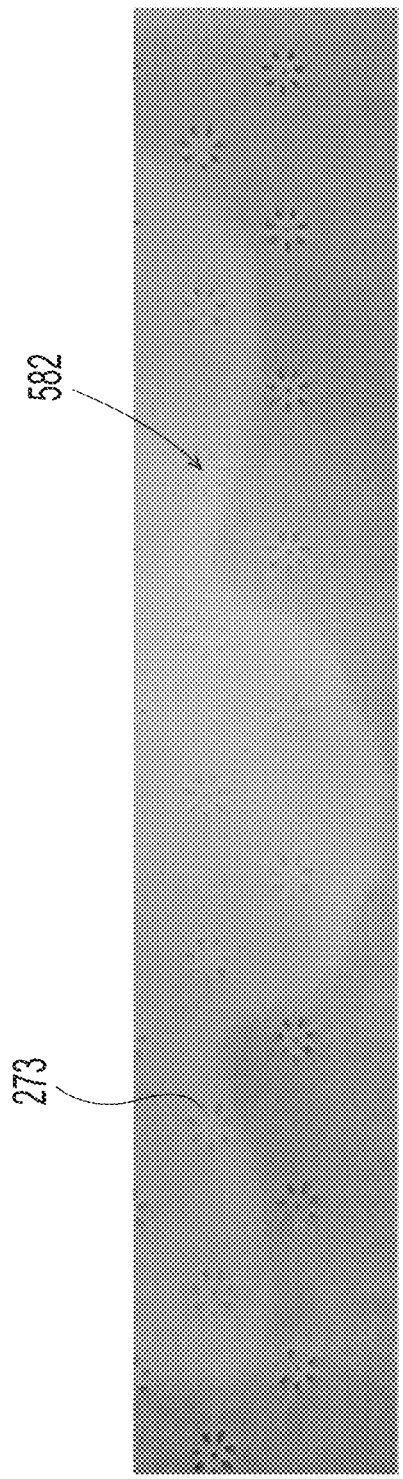
Figure 6B:
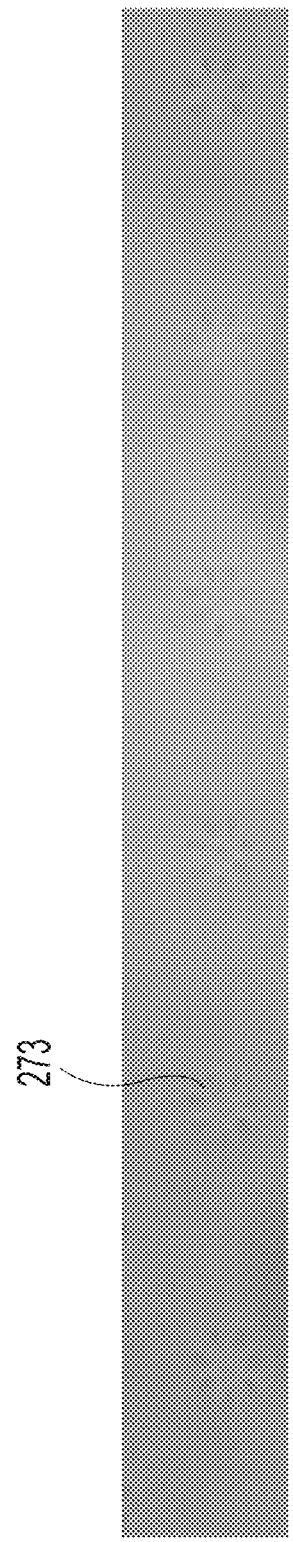

Macro-deformations 273 may be arranged in patterns. An exemplary macro-deformation pattern is shown in FIGS. 6A through 6C. As shown, a plurality of macro-deformations 273 may be arranged in a repeating pattern 633. Additionally, each of the macro-deformations 273 within the repeating pattern 633 may be shaped. For example, as shown in FIG. 6C, a plurality of surrounding macro-deformations 273B may be shaped like flower petals. A central macro-deformation 273A, may be in the shape of a circle. Any suitable shape may be utilized. For example, the macro-deformations 273 may be in the shape of a heart, moon, clouds, sun, rainbows, stars, horseshoes, clovers, bears, the like or combinations thereof.

Additionally, the patterns provided on the material web may comprise a plurality of micro-deformations 263 and a plurality of macro-deformations 273. The micro-deformations 263 may be arranged such that a portion are open and a portion are partially open. The macro-deformations 273 may be shaped as shown and/or described above. And, as shown, the macro-deformations 273 may comprise partially open distal ends. As noted previously, the distal ends 275 may be closed or open. The distal ends of the macro-deformations 273 may comprise a combination of open, partially open, or closed distal ends.

It is also worth noting that while the patterns of macro-deformations 273 are provided in the third zone 320, the patterns of macro-deformations 273 may similarly be provided in the first zone 310 and/or second zone 315 as well. Where patterned macro-deformations 273 are desired in the target area 575 (shown in FIG. 5B), the amount of open area in the distal ends 275 (shown in FIG. 4) can impact fluid acquisition rates. As such, where partially closed distal ends 275 are utilized, additional macro-deformations 273 with open distal ends or higher open area may be required.

Figure 7A:
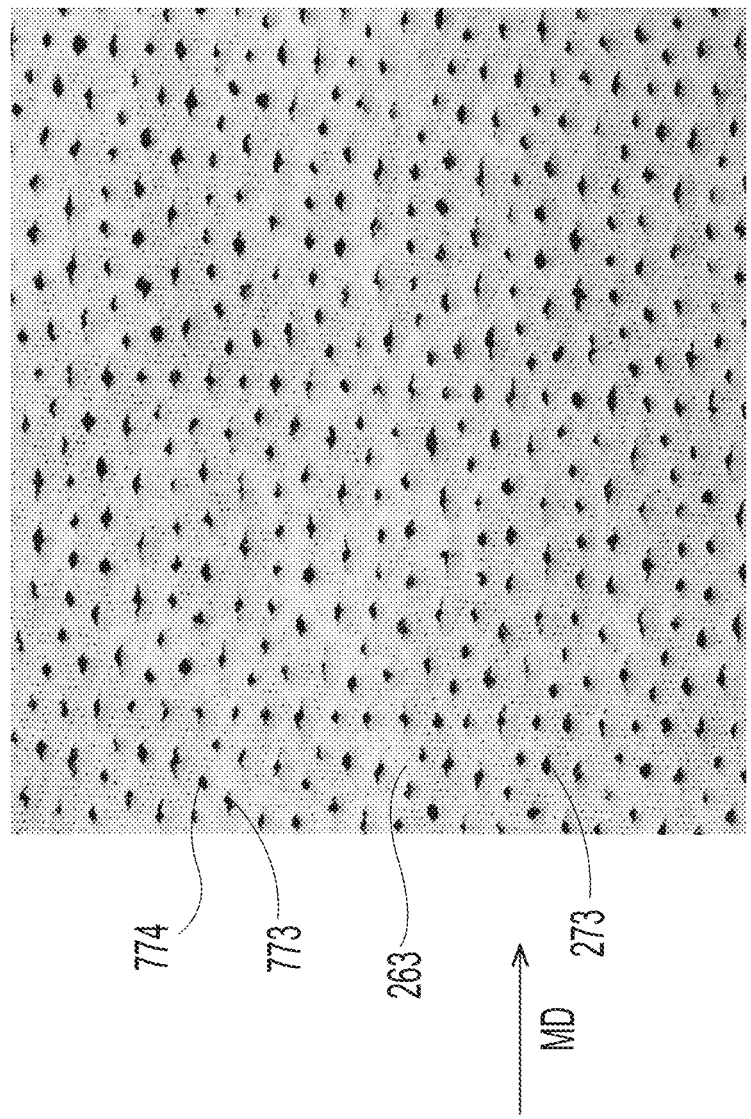

Additional arrangements of macro-deformations are contemplated. Some examples are provided in FIGS. 7A-7C. As shown in FIG. 7A, macro-deformations 273 may be provided in undulating lines in a machine direction ("MD") which provide a wave-like appearance to the macro-deformations 273. In such forms, the macro-deformations 273 may comprise open or partially open distal ends. In order to produce the wave-like appearance, the distal end openings may be varied in size. For example, a wave-like row of larger openings 773 may be adjacent a wave-like row of smaller openings 774. The wave-like row of larger openings 773 may be sandwiched between wave-like rows of smaller openings 774 and vice versa. In some forms, a wave-like row of intermediate openings may be provided between the wave-like rows of larger openings 773 and smaller openings 774. The variation in opening size allows for much easier visualization of the wave pattern. A zig-zag pattern is shown in FIG. 7B. To facilitate the visualization of the zig-zag pattern, larger openings 773 and smaller openings 774 in macro-deformation 273 distal ends may be utilized.

Figure 7C:
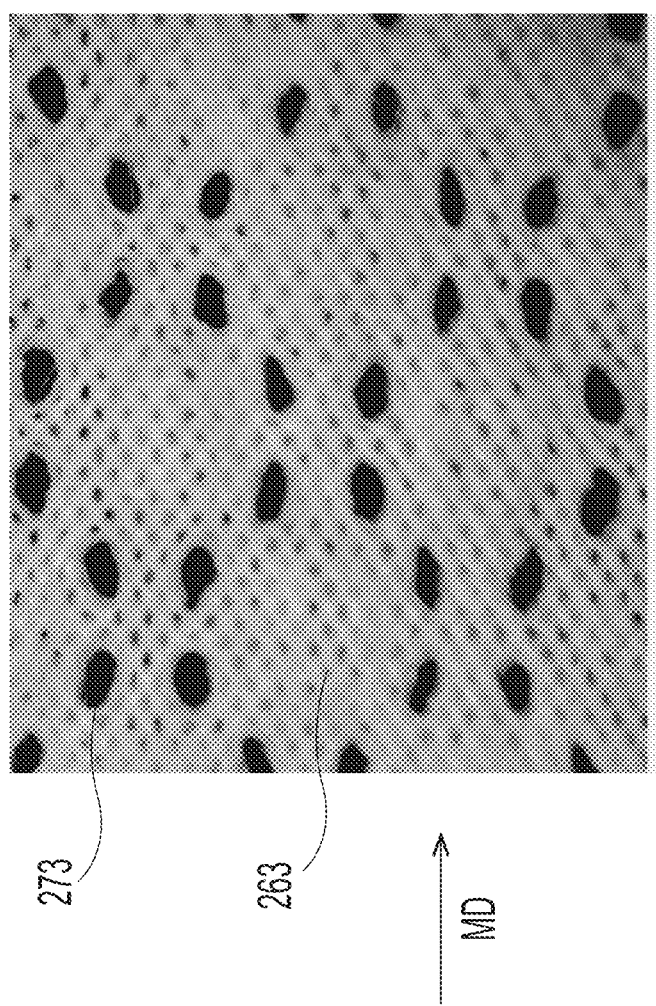

As shown in FIG. 7C, macro-deformations 273 may be arranged in patterns surrounding portions of micro-deformations 263. In some forms, the macro-deformations 273 may comprise open distal ends and/or partially open distal ends. Similarly, as shown, the micro-deformations 263 may comprise open and/or partially open distal ends. Although forms are contemplated where the micro-deformations comprise distal ends which are closed. The closed distal ends of the micro-deformations 263 can be in conjunction with open and/or partially open distal ends or independent thereof.

Macro-deformations 273 are discrete and may be of any suitable configuration. Suitable configurations for macro-deformations 273 include, but are not limited to, features having plan view configurations including circular, oval, hour-glass shaped, star shaped, diamond, polygonal, the like, and combinations thereof. "Polygonal" herein intends to include polygonal with rounded corners. Polygonal shapes include, but are not limited to triangular, quadrilateral, hexagonal, octagonal or trapezoidal. The macro-deformations 273 may be arranged in a staggered pattern. In some forms, the macro-deformations 273 have a plan view substantially quadrilateral such as rectangular, square, and lozenge shape. Lozenge shaped macro-deformations 273 may be provided in a staggered array as the shapes can be well nested and minimize land area 250 (shown in FIG. 2A) between adjacent macro-deformations 273.

The macro-deformations 273 may have a major axis and a minor axis perpendicular to the major axis. The major axis of the macro-deformations 273 may be substantially parallel to the MD of a material web. The major axis of the macro-deformations 273 may be substantially parallel to the CD of the material web. Or, the major axis of the macro-deformations 273 may be oriented at an angle relative to the MD of the material web. Despite the terms of 'major" and "minor" axes, it is intended that a major axis and a minor axis can have an identical length.

A ratio of the major axis to the minor axis can be about 1:1, greater than about 1.1:1, greater than about 1.2:1, greater than about 1.4:1, specifically including all values within these ranges and any ranges created thereby. The macro-deformations may have a major axis that is greater than about 0.5 mm, greater than about 0.8 mm, greater than about 1.0 mm, greater than about 1.2 mm, greater than 1.5 mm, less than about 2.0 mm, specifically including all values within these ranges and any ranges created thereby. The macro-deformations may have a minor axis that is greater than 0.4 mm, greater than 0.5 mm, greater than 0.7 mm, greater than 0.9 mm, greater than 1.0 mm, less than about 1.5 mm, specifically including all values within these ranges and any ranges created thereby.

The plan view area of an individual macro-deformations 273, in some forms may be greater than or equal to about 0.25 $mm^2$, 0.5 $mm^2$, 1 $mm^2$, 5 $mm^2$, 10 $mm^2$, or 15 $mm^2$. The number of macro-deformations 273 per unit area, i.e., the density of macro-deformations 273, can be varied from about 5-60 per/$cm^2$. The material web may comprise macro-deformations 273 with a density of from about 5 to about 60, or from about 10 to about 50, or from about 20 to about 40 per/$cm^2$. As an example, there can be at least 30 macro-deformations/$cm^2$ of material web in the first zone and/or target area. In general, the macro-deformation density need not be uniform across the entire area of the laminate web of the present disclosure, but the macro-deformations 273 can be only in certain regions of the web, such as in regions having predetermined shapes. For example, outboard of the first zone or target area, the density of macro-deformations may decrease.

It is worth noting that the macro-deformations described herein are distinguished from embossments. Embossing involves the compression of a material web between typically two opposing rollers. Generally, one roll comprises male elements which engage a smooth roll. As the web passes between the opposing rollers, the web is compressed between the male elements and the smooth roller.

In contrast, the macro-deformations are deformed via stretching rather than compression. As discussed hereafter regarding the processing of macro-deformations, male and female rolls are utilized to stretching the material web of the present disclosure. As the material web passes between the male and female rolls, the male elements push the material web into the female elements. This pushing of the material web by the male elements into the female elements stretches the material web at a plurality of discrete locations which correspond to the male elements. In general, the macro-deformations of the present disclosure will have a higher air permeability than embossed structures of the same size.

Pre-Cursor Materials

The constituent fibers of the nonwoven web can be comprised of polymers such as polyethylene, polypropylene, polyester, and blends thereof. The fibers can comprise cellulose, rayon, cotton, or other natural materials or blends of polymer and natural materials. The fibers can also comprise a super absorbent material such as polyacrylate or any combination of suitable materials. The fibers can be monocomponent, bicomponent, and/or biconstituent, non-round (e.g., protrusionillary channel fibers), and can have major cross-sectional dimensions (e.g., diameter for round fibers) ranging from 0.1-500 µm. The constituent fibers of the nonwoven precursor web may also be a mixture of different fiber types, differing in such features as chemistry (e.g. polyethylene and polypropylene), components (mono- and bi-), denier (micro denier and >20 denier), shape (i.e. protrusionillary and round) and the like. The constituent fibers can range from about 0.1 denier to about 400 denier. The denier can range from 1 to 100, from 1.2 to 50, from 1.3 to 30, from 1.5 to 15, or 1.8 to 6, specifically including all values within these ranges and any ranges created thereby.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

As used herein, the term "non-round fibers" describes fibers having a non-round cross-section, and includes "shaped fibers" and "protrusionillary channel fibers." Such fibers can be solid or hollow, and they can be tri-lobal, delta-shaped, and are preferably fibers having protrusionillary channels on their outer surfaces. The protrusionillary channels can be of various cross-sectional shapes such as "U-shaped", "H-shaped", "C-shaped" and "V-shaped".

A nonwoven layer may comprise fibers having sufficient elongation properties to have portions elongated. The portion elongated are formed by urging fibers out-of-plane in the Z-direction at discrete, localized, portions of the nonwoven layer. The urging out-of-plane can be due to fiber displacement, i.e., the fibers are able to move relative to other fibers and be "pulled," so to speak, out-of-plane. More often, however, for most nonwoven layers suitable for the laminate according to the present invention, the urging out-of-plane is due to the fibers having been at least partially plastically stretched and permanently deformed.

The nonwoven layer useful for the material web according to the present disclosure can comprise a nonwoven web comprised of substantially randomly oriented fibers. By "substantially randomly oriented" is meant that, due to processing conditions for producing the precursor nonwoven web, there may be a higher amount of fibers oriented in the MD than the CD, or vice-versa.

The nonwoven layer may have a basis weight of between about 6 gsm to about 60, between about 8 gsm and about 25 gsm, or between 10 gsm to about 18 gsm, specifically including all values within these ranges and any ranges created thereby. In general, nonwoven, especially spunbond nonwoven, of higher basis weight reduces acquisition speed though it may increase stain masking.

Useful nonwoven layers of the present disclosure comprise a median distance between two adjacent fibers in a z-direction of above about 55 µm, or in the range of about 60 to about 200 µm, when measured according to the Fiber-Fiber Distance Measurement described in the present specification. When the nonwoven layer comprises carded nonwoven, the carded nonwoven can be produced to have a median distance between two adjacent fibers in a z-direction of above about 55 µm by optimizing production conditions such as oven air flow temperature, hot air pressure, and nonwoven web tension when the web goes through the oven and/or calendar rolls to increase a caliper of the nonwoven. For example, the higher oven air flow temperature, the lower caliper of the nonwoven, and the higher hot air pressure, the lower caliper for the nonwoven. In addition, a tighter web tension may result in a lower caliper of the nonwoven. In one example, the nonwoven web is carded nonwoven formed from a polymer having a fiber thickness of no less than 5 denier.

Some specific examples of nonwoven layer which are suitable for the material webs of the present disclosure include: (1) 10 gsm spunbond with hydrophilic polypropylene fibers; (2) 15 gsm carded, air-through bonded nonwoven with 6 denier polypropylene fibers; and (3) 15 gsm carded, air-through bonded nonwoven with 3 denier polypropylene fibers.

In some specific examples, the nonwoven layer of the material web may comprise a plurality of bi-component fibers. The fibers may be staple length and may comprise a core-sheath configuration. The sheath may comprise polyethylene and the core may comprise polyethylene terephthalate. Crimped fibers may be utilized as desired to provide additional loft to the material web which can result in a softer, more cushiony feel for the wearer of an absorbent article incorporating the material web.

The film layer may comprise a constituent material that comprises a polyolefin. The film layer may have a basis weight of between about 8 gsm to about 35 gsm, between about 10 gsm to about 20 gsm, or between about 12 gsm to about 15 gsm, specifically reciting all values within these ranges and any ranges created thereby. If the film layer has a basis weight more than 35 gsm, desirable softness of the composite/laminate may not be obtained. If the film has a basis weight less than 8 gsm, it may tear during wearing of the absorbent article.

The film layer may have sufficiently high elongation properties such as stretchability relative to the nonwoven layer at a process temperature, especially at the temperature in a protrusion forming step described in detail below, such that upon experiencing the strain of constituent material being urged out-of-plane in the positive and/or negative Z-direction, the film layer does not break or rupture, e.g., by tearing due to extensional failure.

One specific example of a film which is useful in the material webs of the present disclosure comprises 100 percent polyethylene. Specifically, the film may comprise about 50 percent low density polyethylene by weight, about 23 percent high density polyethylene by weight, about 20 percent linear low-density polyethylene by weight, and about 7 percent by weight titanium dioxide. Any suitable combinations of polyethylene, low density polyethylene, linear-low density polyethylene, high density polyethylene, copolymers thereof, block copolymers, and polyethylene and polypropylene co polymers.

The material webs of the present disclosure may have any suitable thickness. Some suitable thicknesses include about 0.65 mm under 0.2 psi for those material webs which comprise an air-through bonded nonwoven layer. For the material webs which utilize a spunbond nonwoven layer, the thickness may be about 0.6 mm under 0.2 psi. Without macro deformations, the thicknesses may decrease to about 0.35 mm under 0.2 psi foot pressure.

Process

A discussion of the differences between a laminate material web and a composite material web are provided herein. Recall that prior to the formation of the micro-deformations, the nonwoven layer and film layer may be combined via any suitable lamination methods known, e.g. adhesives, bonding, etc. This can allow for the micro-deformation processes and macro-deformation processes—discussed herein—to be applied to both the nonwoven layer and the film layer simultaneously. Or, the film layer may go through the micro-deformation process and/or the macro-deformation process prior to being laminated with the nonwoven layer, or vice versa.

Additionally, composite material webs can allow the micro-deformation processes and the macro-deformation process to be applied to the composite material web simultaneously. Recall that for the composite material web, the polymeric film material may be extruded onto the nonwoven layer or nonwoven layers. Due to the softened state of the polymeric film, it is believed that the film layer flows into interstices between the nonwoven layer fibers thereby reducing or even eliminating the need for the use of adhesives or other bonding mechanisms.

A variety of processes may be utilized to form the micro-deformations of the present disclosure. For example, when the micro-deformations are discrete extended elements with open distal ends, the discrete extended elements may be formed by applying high pressure vacuum against the forming surface of the forming member that the formed web ply is against. Such methods of aperturing are known as "Vacuum Forming" and are described in greater detail in U.S. Pat. No. 4,463,045. Examples of mechanical deformation is disclosed in U.S. Pat. Nos. 4,798,604, 4,780,352, 3,566,726, 4,634,440, WO 97/40793, and European Patent 525,676. Examples of flocking are disclosed in WO 98/42289, WO 98/36721, and European Patent 861,646. Examples of ultrasonics are disclosed in U.S. Pat. No. 5,269,981. Examples of delamination of viscous melts are disclosed in U.S. Pat. No. 3,967,623, and WO 99/06623. Examples of printed hair are disclosed in U.S. Pat. No. 5,670,110. Examples of brushing are disclosed in WO 99/06623. Other suitable processes which may be utilized in the formation of micro-deformations include hydroforming as described in U.S. Patent Application Publication No. US2003/0003269 A1. Additionally, forms are contemplated where micro-deformations are formed via a first process and the macro-deformations are formed via a second process which is different than the first process. Some examples of varied processing are disclosed in U.S. Patent Application Publication No. US2003/0003269 A1.

The formation of the macro-deformations may similarly comprise a variety of manufacturing options. For example, where the distal ends of the macro-deformations are open, vacuum-forming, hydro-forming, hot pin aperturing, etc. may be utilized. It is worth noting however, that the process for forming the macro-deformations should be selected carefully. Where the micro-deformations form a portion of a wearer-facing surface of an article, subsequent processing to form the macro-deformations may damage the micro-deformations. Such damage to the micro-deformations can detrimentally affect perceived softness of the material web. In one particular form—which preserves the majority of micro-deformations in land areas between macro-deformations—mechanical deformation with controlled engagement with the material web can be utilized. For example, an apparatus that may comprise any suitable type(s) of forming structure, e.g. a pair of rolls that define a nip therebetween; pairs of plates; belts, etc. Additionally, it is believed that a mechanical aperturing process utilizing forming structures, e.g. a pair of rolls, reduces the likelihood that nonwoven fibers are pushed through the film layer. This may be beneficial for fluid acquisition as described herein. In contrast, hydroforming is believed to encourage nonwoven fibers to be pushed through the film layer through the macro-deformations.

Using an apparatus with rolls can be beneficial in the case of continuous processes, particularly those in which the speed of the process is of interest. Although the apparatuses will be described herein for convenience primarily in terms of rolls, it should be understood that the description will be applicable to forming structures comprising a forming member that have any other suitable configurations.

The rolls for a mechanical deformation process forming macro-deformations described herein are typically generally cylindrical. The term "generally cylindrical", as used herein, encompasses rolls that are not only perfectly cylindrical, but also cylindrical rolls that may have elements on their surface. The term "generally cylindrical" also includes rolls that may have a step-down in diameter, such as on the surface of the roll near the ends of the roll. The rolls are also typically rigid (that is, substantially non-deformable). The term "substantially non-deformable", as used herein, refers to rolls having surfaces (and any elements thereon) that typically do not deform or compress under the conditions used in carrying out the processes described herein. The rolls can be made from any suitable materials including, but not limited to steel, aluminum or rigid plastic. The steel may be made of corrosion resistant and wear resistant steel, such as stainless steel. At least one of the rolls may or be heated. If heated, consideration of thermal expansion effects must be accommodated according to well-known practices to one skilled in the art of thermo-mechanical processes.

The rolls for a mechanical deformation process forming macro-deformations described herein have surfaces which may be provided with forming elements comprising: male elements such as discrete projections such as teeth; female elements such as recesses such as discrete voids in the surface of the rolls; or any suitable combination thereof. The female elements may have a bottom surface (which may be referred to as depressions, or cavities), or they may be in the form of apertures (through holes in the surface of the rolls). In some forms, the forming elements on the members such as the rolls of the forming unit may comprise the same general type (that is, the opposing components may both have male and female elements thereon, or combinations of male and female elements). The forming elements may have any suitable configuration. One type of male elements useful in the formation of macro-deformations described herein include teeth having a base in a generally polygonal shape such as octagonal, hexagonal and quadrilateral shape, and having a cross-sectional length and a cross-sectional width. The teeth can have any suitable aspect ratio of its cross-sectional length to its cross-sectional width to form macroscopic structures, in a web. For example, the teeth can have a generally hexagonal shape base or a generally quadrilateral shape base. The male elements can have tips that are flat, rounded or sharp. As noted previously, the macro-deformation distal ends may comprise stretched micro-deformations, closed micro-deformations, or apertures. In general, sharper male elements create apertures in the macro-deformation distal ends. Flat tips can create the stretched micro-deformations in the sidewalls and closed or same size micro-deformations in the distal end, while rounded tips can create stretched/enlarged micro-deformations in the distal ends. Additionally, rounded or sharper male elements can help to displace filaments/fibers from the distal ends of the macro-deformations which is believed to benefit fluid acquisition.

In certain forms, the shapes of the female elements may differ from the shapes of any mating male elements. In some forms, the female elements can be configured to mate with one or more male elements.

Figure 8:
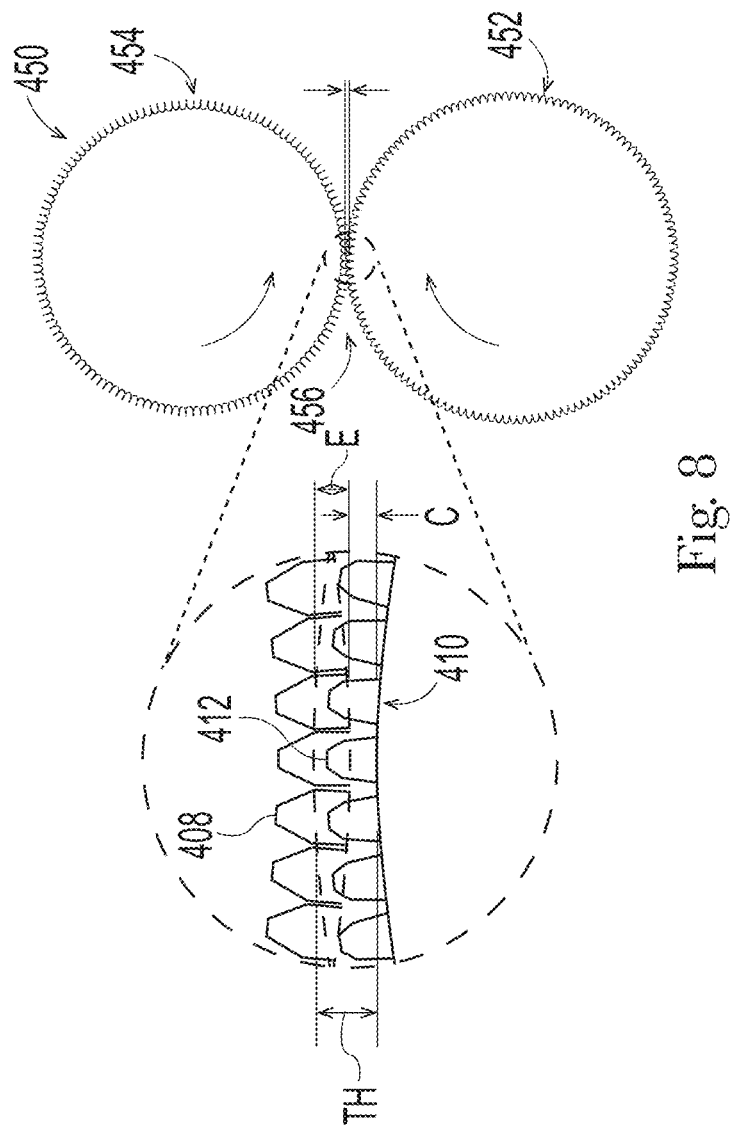
FIG. 8 is a schematic representation of an apparatus for producing the webs of the present disclosure.

FIG. 8 shows in more detail the portion of an exemplary forming unit 450 for creating some of the macro-deformations described herein. Forming unit 450 comprises a pair of intermeshing rolls 452 and 454 rotating in opposite directions. Forming unit 450 can be designed such that the material web remains on roll 452 through a certain angle of rotation. The forming step may be carried out in a process speed not causing ruptures or tearing in the macro-deformations. The process speed may be determined considering stretchability of the film at the process temperature. During formation of the macro-deformations, the material web may be stabilized by heat-setting. Once out of the nip 456, specifically, the film layer may be heat-set to the shape of the macro-deformations so that the film layer does not recover back to its original shape such as a flat sheet or close to the original shape. The heat-set may be conducted by resting over the material web on teeth 410 of heated roll 452 at or near the softening point of the film. The heat-set temperature is preferably in the range of ±5° C. of a softening point temperature of the film.

The term "softening point temperature", as used herein, represents a material temperature that is between 70% and 99% of the melt point of the material. For example, if a material, regardless of whether it is an alloy, a composite, or a pure element, has a stated melt point of 100 degrees Celsius, then the softening point temperature of the material is 70 degrees Celsius to 99 degrees Celsius.

The first roll 452 comprises a plurality of first male elements. As shown, the plurality of first male elements may be formed as rows of circumferentially-spaced teeth 410 that extend in spaced relationship about at least a portion of roll 452. Teeth 410 can be arranged in a staggered pattern. Teeth 410 may extend radially outwardly from the surface of the roll 452 to engage depressions 408 of roll 454. The engagement of the teeth 410 and the depressions 408 is shown in greater detail in the cross-sectional representation of FIG. 8, discussed below. Both or either of rolls 452 and 454 can be heated by means known in the art such as by incorporating hot oil filled rolls or electrically-heated rolls. Alternatively, both or either of the rolls may be heated by surface convection or by surface radiation.

At any cross-sectional location parallel to the base of each tooth can have a round or a non-round cross-sectional area. In an alternate embodiment, the teeth may comprise pins that are rectangular or other shapes depending on the corresponding second element shape desired.

The second roll 454 can comprise a plurality of first female elements. As shown, the plurality of first female elements can be discrete depressions 408 into which one or more of teeth 410 of roll 452 mesh. The depression 408 may have the same shape as a base of the teeth 410 and slightly larger dimensions on all edges and side than the base of the teeth 410. The depth of the depressions 408 may be deeper than a height of the teeth 410. The grooves 408 may or may not be tapered. In the case, the spacing of second elements is limited by the spacing of the depressions 408 on roll 454. A center-to-center distance of two adjacent teeth is a measure between centers of two adjacent teeth. A point where a major axis and a minor axis of a tooth cross each other is determined as the center of the tooth.

Still referring to FIG. 8, as shown teeth 410 have tooth height TH, depth of engagement E, and gap clearance C. A tooth height TH may range from about 0.5 mm to about 10 mm Depth of engagement E is a measure of the level of engaging rolls 452 and 454 and is measured from a top surface of the roll 454 to top 412 of tooth 410 of the roll 452. Gap clearance C is a distance between a top surface of the roll 454 and a bottom surface of the roll 452 when rolls 452 and 454 are in maximum engagement. Gap clearance is preferably wide enough to prevent the micro-deformations, especially when the micro-deformations are discrete extended elements formed in a precursor web, from incurring heat induced damage due to the macro-deformation forming step. This precaution allows the micro-deformations to remain substantially intact during the macro-deformation formation process which helps preserve softness as well as fluid handling of the web.

Gap clearance preventing from heat-induced damage can be determined based on material web thickness, height of micro-deformations, macro-deformation formation process operation conditions such as roll temperature and production speed.

The size, shape, orientation and spacing of the teeth 410 can be varied about the circumference and width of roll 452 to provide for varied material web properties and characteristics. For example, as noted regarding FIGS. 5A and 5B, the micro-deformations and macro-deformations may be provided in zones. Referring now to FIGS. 5A, 5B, 8, and 9, to provide zones in a resultant material web, the rolls 452 and 454 may similarly comprise zones. Teeth 410 which correspond to the first zone 310 may comprise a sharp tooth top 412 to create open or partially open distal ends in corresponding macro-deformations. In contrast, teeth 410 which correspond to the second zone 315 and third zone 320, may comprise more rounded or flat tooth tops 412 to create partially open or closed distal ends in corresponding macro-deformations. In such forms, the partially open distal ends of macro-deformations in the second zone 315 and third zone 320 may be less open than the macro-deformations of the first zone 310. Additionally, the teeth 410 and corresponding depressions 408 in the second zone 315 and third zone 320 may have a lower depth of engagement than the teeth 410 and depressions 408 which correspond to the first zone. Additional zonal configurations for absorbent articles are contemplated. Some suitable zones are described in U.S. Pat. Nos. 8,569,572 and 9,872,801.

The lower depth of engagement can minimize the stretching of the distal ends of the macro-deformations which can create a closed or less open distal end. In some forms, teeth 410 which correspond to the first zone 310 may comprise a rounded or flat tooth tip 412. In such forms, a higher depth of engagement between the rounded or flat tipped teeth 410 and depressions 408 may be utilized. This can produce stretching in the distal ends of the macro-deformations which can cause the micro-deformations on the distal end to expand which can aid in fluid acquisition.

Figure 10:
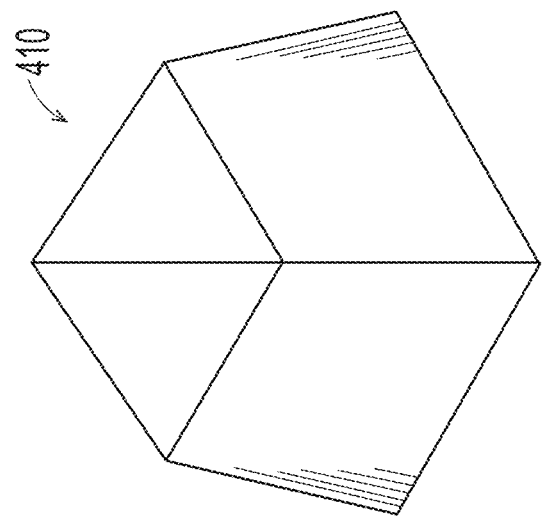
FIGS. 9-10 are schematic representations of teeth shapes which can produce the webs in accordance with the present disclosure.
Figure 9:
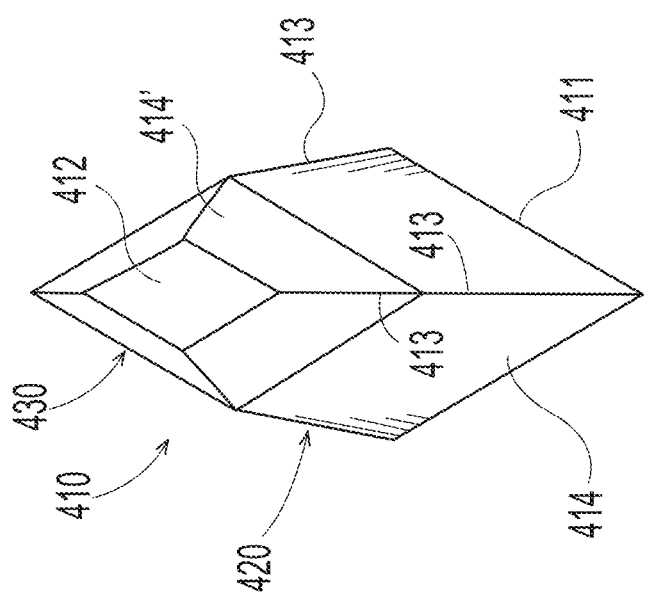

Perspective views of exemplary configuration for tooth 410 are shown in FIGS. 9 and 10. As shown in FIG. 9, each tooth 410 has a base 411, a tooth top 412, edges 413 and sides 414. Edges 413 and sides 414 may be slightly rounded. Teeth 410 can have a base in a generally polygonal shape. For example, at their base 411, the cross section of teeth 410 can have a tooth cross-sectional length TL and a tooth cross-sectional width TW exhibiting a tooth aspect ratio AR of TL/TW of not greater 3.3, or not greater than 2.5, or not greater than 2, or not greater than 1.9. In some forms, each of the teeth has a quadrilateral shape base. The teeth 410 are tapered from the base to the top. In some forms, a degree of taper may not be constant along the height of the teeth shown in FIG. 9. In other forms, a degree of taper may be constant along the height of the teeth. The tooth 410 may comprise a proximal part 420 joined to a member of a forming unit, and a distal part 430 directly adjacent to the proximal part and tapering to a tooth top 412. The tooth 410 may comprise a proximal part, a distal part, and a middle part between the proximal part 420 and the distal part 430. The proximal part and the distal part may have different degree of taper from each other. In some forms, the distal part 430 has a higher degree of taper than the proximal part 420. In some forms, at least one of the proximal part 420 and the distal part 430 has a constant degree of taper. The proximal part is generally a frustum shape tapering from a polygonal-shape base to a point. As shown in FIG. 9, a proximal part 420 can have four sides 414, each side being generally (isosceles) rectangular. The vertex of two sides makes up an edge. The vertices of edges 413 can be machined to have a rounded radius of curvature. As shown in FIG. 9, a distal part 430 can have a generally rectangular shape having at least four sides 414', each side being substantially triangular and tapering from the bottom of the distal part to a tip of the tooth. The vertex of two sides of the distal part 430 makes up an edge. The vertices of edges 413' can be relatively sharp or can be machined to have a rounded radius of curvature. The tooth top 412 can be flat, or otherwise slightly shaped so as to stretch but not to puncture the material web. In some forms, a flat tooth top 412 can transition to sides 414 and the transition can be at a radius of curvature, providing for a smooth, rounded, flat tooth top. Without being bound by theory, it is believed that having relatively a smooth, rounded, flat tooth top permits the teeth 410 to form macro-deformations without resulting in apertures or tearing in the macro-deformations. FIG. 10 is another exemplary tooth for the formation of macro-deformations in a material web for use in the forming unit.

Referring to FIGS. 8-10, it is worth noting that the forming unit 450 is not an embossing process. As noted previously, embossing generally involves the compression of materials in a nip between two rolls. In contrast to embossing, the teeth 410 of the rolls of the present description, specifically the tooth tips 412 are not required to engage a bottom of the depressions 408. If desired, tooth tips 412, or a portion thereof may engage the bottom of the depressions 408. With such configurations, the distal ends of the macro-deformations may be closed, and the material web would be compressed in those corresponding macro-deformations.

Figure 11A:
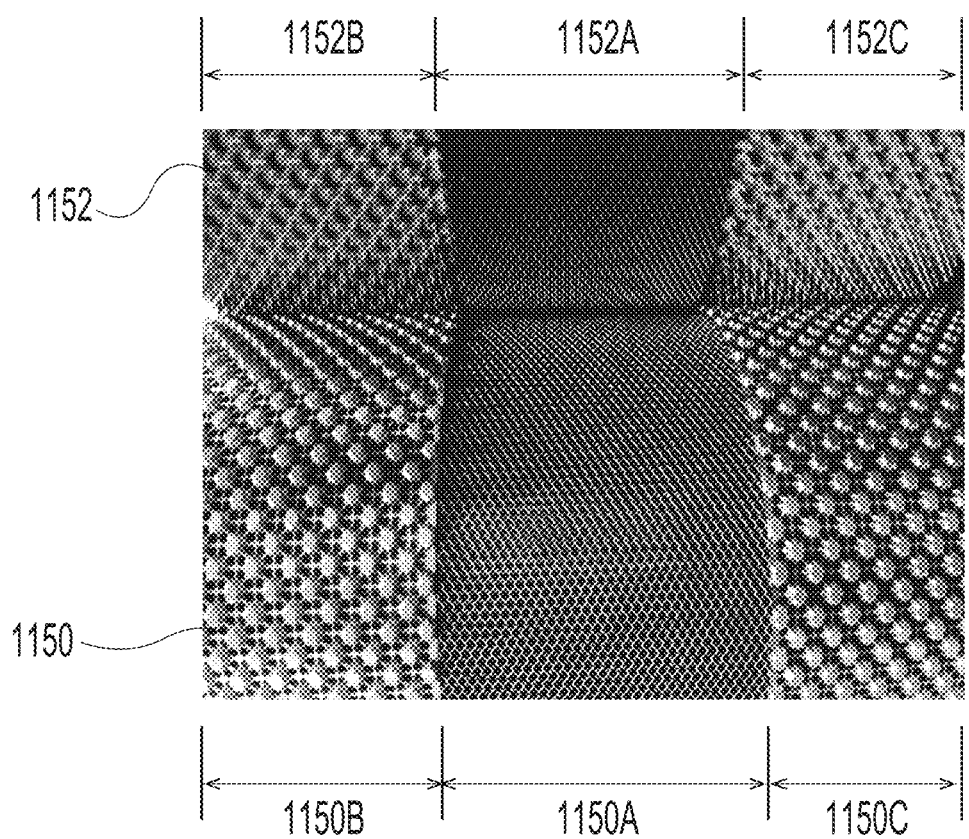
FIG. 11A is a photograph showing a close up view of surfaces of a male/female roll arrangement with zones thereon.
Figure 11B:
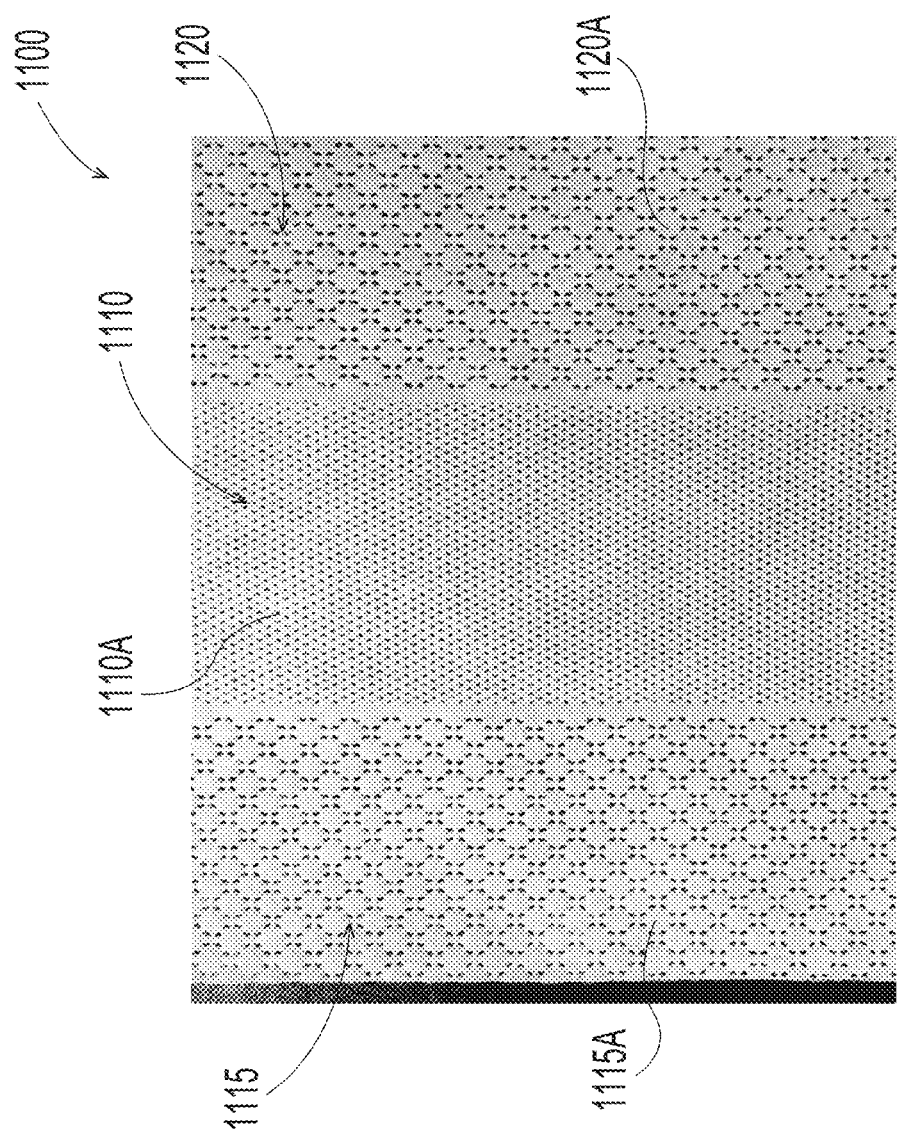
FIG. 11B is a photograph showing a close up view of a web constructed from the rolls shown in FIG. 11A.

Some exemplary patterns for rolls and material webs are shown regarding FIGS. 11A and 11B. As shown, a first roll 1150 and a second roll 1152 may comprise multiple zones. A first zone 1150A of the first roll 1150 may correspond to a first zone 1152A of the second roll 1152. In order to provide good fluid drainage, the first zone 1152A of the second roll 1152 may comprise a plurality of male elements that engage a plurality of corresponding female elements in the first zone 1150A of the first roll 1150. Conversely, second and third zones 1150B and 1150C, respectively, of the first roll 1150 may comprise a plurality of male elements which engage a plurality of corresponding female elements in a second and third zone 1152B and 1152C, respectively, of the second roll 1152.

Based on the rolls shown, the zones in the resultant material web may be created contemporaneously. However, rolls and processing are contemplated where the zones are created sequentially.

A resultant material web 1100 is shown in FIG. 11B. As shown, the material web 1100 comprises a first zone 1110 which corresponds to the first zones 1150A and 1152A of the first and second rolls 1150 and 1152, respectively. The material web 1100 further comprises a second zone 1115 which corresponds to the second zones 1150B and 1152B of the first roll 1150 and the second roll 1152, respectively. The material web 1100 further comprises a third zone 1120 which corresponds to the third zones 1150C and 1152C of the first roll 1150 and second roll 1152, respectively.

Where the first roll 1150 and the second roll 1152 comprise both male and female elements, the structure of the material web 1100 can be configured to provide a variety of functions. The first zone 1110 of the material web 110 may comprise a plurality of apertures which allow good fluid acquisition. However, because the first zone 1152A of the second roll comprises male elements which engage female elements of the first zone 1150A of the first roll, the apertures may comprise sidewalls which extend perpendicular (into) the drawing sheet. Conversely, pillows 1115A and 1120A of the second zone 1115 and third zone 1120 of the material web 1100 may extend perpendicular (out) of the drawing sheet. This may be due to the first roll 1150 in the second zone 1150B and third zone 1150C comprising male elements which engage female elements in the corresponding second zone 1150B and third zone 1150C of the second roll 1152. The pillows 1115A and 1120A can help provide a cushiony-soft feel for the user.

Another suitable pattern for a material web is shown with regard to FIG. 12. As shown, a first roll 1250 may engage/intermesh with a second roll 1252. As shown, the first roll 1250 may comprise a first zone 1250A which corresponds to a first zone 1252A on the second roll 1252. The first zone 1252A of the second roll 1252 may comprise a plurality of male elements which engage a plurality of corresponding female elements in the first zone 1250A of the first roll 1250. The first roll 1250 further comprises a second zone 1250B and a third zone 1250C. Similarly, the second roll 1252 may comprise a second zone 1252B and a third zone 1252C. As shown, the second zone 1252B of the second roll 1252 may comprise a plurality of male elements which engage with a plurality of corresponding female elements in the second zone 1250B of the first roll 1250. The third zone 1252C of the second roll 1252 may comprise a plurality of male elements which engage with a plurality of corresponding female elements in the third zone 1250C of the first roll 1250.

The male elements in the second zone 1252B and third zone 1252C of the second roll 1252 can have varying depths of engagement. The corresponding female elements in the second zone 1250B and third zone 1250C in the first roll 1250 may similarly be configured. For example, taller male elements may correspond with deeper female elements such that any structures created are not compressed between the male and female elements of the first roll and the second roll. Or, embossing may be desired for some portions of the material web. In such instances, female and male elements may be configured such that compression of the material web occurs. However, as noted previously, embossing reduces the level of permeability of the material web. This should be noted when utilizing embossing. And, embossments and any embossing processes are not included in macro-deformations or macro-deformation processes.

Rolls can be created where the zones comprise a mixture of male and female elements. For example, a first zone of a first roll may be configured with both male and female elements which engage with corresponding female and male elements of a first zone on a second roll. The second zones and third zones may be similarly configured. This configuration of the rolls can provide fluid acquisition in the first zone including the target area and may provide a soft-cushiony feel in the first, second, and third zones, as well.

The provision of micro-deformations and/or macro-deformations can be provided by a variety of parties. For example, the micro-deformations may be provided in the film layer(s) from a supplier and subsequently the film layer(s) are provided to an absorbent article manufacturer. The absorbent article manufacturer can then process the film layer(s) with one or more nonwoven layers to form the material web. The manufacturer may then provide additional micro-deformations described herein and/or macro-deformations described herein to the material web. Subsequently, the manufacturer can convert the material web into absorbent articles by adding an absorbent system and backsheet.

As another example, the material web, including film layer(s) and nonwoven layer(s) may be provided to an absorbent article manufacturer from a supplier. In such instances, the micro-deformations and/or macro-deformations may be provided by the supplier either to the film layer(s) or to the material web overall. The absorbent article manufacturer may then further convert the material web into absorbent articles by adding an absorbent system and backsheet. Or, the manufacturer may choose to provide additional micro-deformations and/or macro-deformations and then subsequently convert the material web into absorbent articles. The supplier may choose to extrude the film directly onto the nonwoven material thereby forming a composite material web. Or the supplier may choose to extrude the film separately from the nonwoven material and subsequently combine the two layers, e.g. film layer and nonwoven layer, to form a laminate material web.

Yet another example, a supplier may provide the absorbent article manufacturer with the material web with no micro-deformations and/or no macro-deformations. The manufacturer may then provide micro-deformations and/or macro-deformations to the material web and then subsequently convert the material web into absorbent articles. Much like the above example, the material web may be a laminate material web or a composite material web depending on how the supplier manufactures the material web.

Yet another example, a manufacturer may choose to create at least one of the film layer(s) and/or nonwoven layer(s) online, i.e. within the converting process and provide the micro-deformations and macro-deformations as described herein. Subsequently, the manufacturer may then convert the material web into absorbent articles. The manufacturer may choose to extrude the film directly onto the nonwoven material thereby forming a composite material web. Or, the manufacturer may choose to extrude the film separately from the nonwoven material and subsequently combine the two layers, e.g. film layer and nonwoven layer, to form a laminate material web.

Absorbent Articles

The material webs of the present disclosure may form any suitable portion of a disposable absorbent article. In some forms, as noted previously, the material web may form a portion of the topsheet. In such forms, the material web may form a portion of a wearer-facing surface of the absorbent article. The film layer may form a portion of the wearer-facing surface or the nonwoven material may form a portion of the wearer-facing surface of the absorbent article. Some suitable examples of absorbent articles which may benefit from the user of the material webs described herein include diapers, including taped diapers—refastenable; diaper pants—pre-fastened refastenable or pre-fastened non-refastenable; feminine sanitary napkins; tampons; adult incontinence products, e.g. pants or pads; baby wipes, sanitary wipes, cleansing wipes, and/or the like.

Referring to FIG. 13, an absorbent article 1810 which may utilize the material webs described herein may be a sanitary napkin/feminine hygiene pad. As shown, the sanitary napkin 1810 may comprise a liquid permeable topsheet 1814, a liquid impermeable, or substantially liquid impermeable, backsheet 1816, and an absorbent core 1818 positioned intermediate the topsheet 1814 and the backsheet 1816. The sanitary napkin 1810 may comprise wings 1820 extending outwardly with respect to a longitudinal axis 1880 of the sanitary napkin 1810. The sanitary napkin 1810 may also comprise a lateral axis 1890. The wings 1820 may be joined to the topsheet 1814, the backsheet 1816, and/or the absorbent core 1818. The sanitary napkin 1810 may also comprise a front edge 1822, a rear edge 1824 longitudinally opposing the front edge 1822, a first side edge 1826, and a second side edge 1828 laterally opposing the first side edge 1826. The longitudinal axis 1880 may extend from a midpoint of the front edge 1822 to a midpoint of the rear edge 1824. The lateral axis 1890 may extend from a midpoint of the first side edge 1826 to a midpoint of the second side edge 1828. The sanitary napkin 1810 may also be provided with additional features commonly found in sanitary napkins as is known in the art. In some forms of the present invention, the wings may be provided with zones of extensibility as described in U.S. Pat. No. 5,972,806.

Any suitable absorbent core known in the art may be utilized. The absorbent core 1818 may be manufactured from a wide variety of liquid-absorbent materials commonly used in disposable absorbent articles such as comminuted wood pulp which is generally referred to as airfelt. The absorbent core 1818 may comprise superabsorbent polymers (SAP) and less than 15%, less than 10%, less than 5%, less than 3%, or less than 1% of airfelt, or be completely free of airfelt. Examples of other suitable absorbent materials comprise creped cellulose wadding, meltblown polymers including coform, chemically stiffened, modified or cross-linked cellulosic fibers, tissue including tissue wraps and tissue laminates, absorbent foams, absorbent sponges, superabsorbent polymers, absorbent gelling materials, or any equivalent material or combinations of materials.

The configuration and construction of the absorbent core 1818 may vary (e.g., the absorbent core may have varying caliper zones, a hydrophilic gradient, a superabsorbent gradient, or lower average density and lower average basis weight acquisition zones; or may comprise one or more layers or structures). In some forms, the absorbent core 1818 may comprise one or more channels, such as two, three, four, five, or six channels.

The absorbent core 1818 of the present disclosure may comprise one or more adhesives, for example, to help immobilize the SAP or other absorbent materials within a core wrap and/or to ensure integrity of the core wrap, in particular when the core wrap is made of two or more substrates. The core wrap may extend to a larger area than required for containing the absorbent material(s) within.

Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen.

Other forms and more details regarding channels and pockets that are free of, or substantially free of absorbent materials, such as SAP, within absorbent cores are discussed in greater detail in U.S. Patent Application Publication Nos. 2014/0163500, 2014/0163506, and 2014/0163511, all published on Jun. 12, 2014.

The absorbent article 1810 may comprise additional layers between the topsheet 1814 and the absorbent core 1818. For example, the absorbent article 1810 may comprise a secondary topsheet and/or an acquisition layer positioned between the topsheet 1814 and the absorbent core 1818.

The backsheet can comprise a liquid impervious film. The backsheet can be impervious to liquids (e.g., body fluids) and can be typically manufactured from a thin plastic film. However, typically the backsheet can permit vapours to escape from the disposable article. A suitable microporous polyethylene film is manufactured by Mitsui Toatsu Chemicals, Inc., Nagoya, Japan and marketed in the trade as PG-P.

The backsheet can be typically positioned adjacent an outer-facing surface of the absorbent core and can be joined thereto by any suitable attachment device known in the art. For example, the backsheet may be secured to the absorbent core by a uniform continuous layer of adhesive, a patterned layer of adhesive, or an array of separate lines, spirals, or spots of adhesive. Illustrative, but non-limiting adhesives, include adhesives manufactured by H. B. Fuller Company of St. Paul, Minn., U.S.A., and marketed as HL-1358J. Some examples of a suitable attachments are disclosed in U.S. Pat. Nos. 4,573,986; 3,911,173; 4,785,996; and 4,842,666. Alternatively, the attachment device may include heat bonds, thermal fusion bonds, pressure bonds, ultrasonic bonds, dynamic mechanical bonds, or any other suitable attachment device or combinations of these attachment devices. The backsheet may be additionally secured to the topsheet by any of the above-cited attachment devices/methods.

Still another example of a disposable absorbent article which may utilize the material webs of the present invention are diapers which include non-refastenable pants, re-fastenable pants and/or re-fastenable diapers. Diapers have can have a similar construction to that of sanitary napkins. An exemplary diaper is described below.

Figure 14:
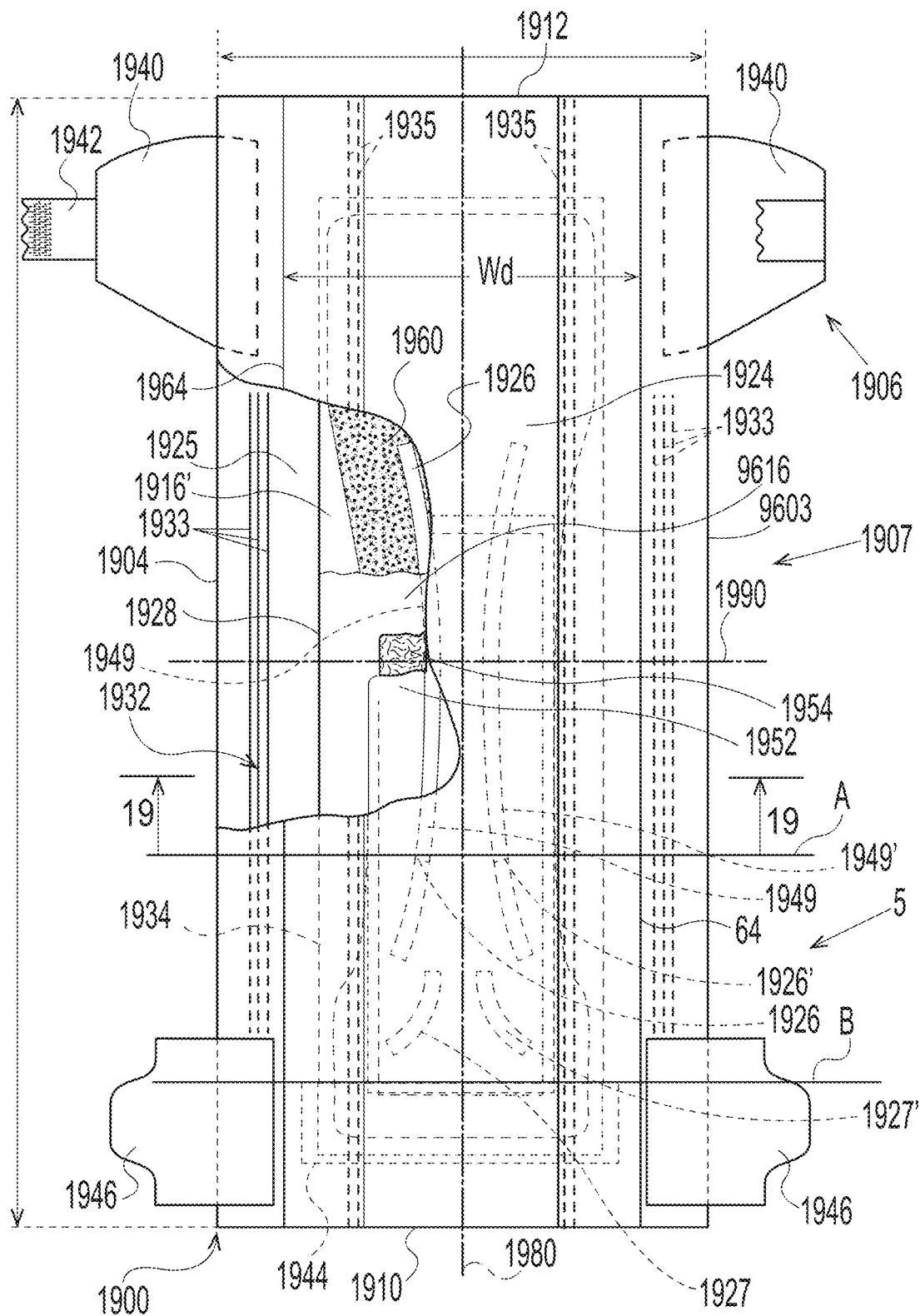
FIG. 14 is a schematic representation of a diaper constructed in accordance with the present disclosure.

Referring to FIG. 14, a plan view of an example absorbent article that is a diaper 1900 in its flat-out, uncontracted state (i.e., with elastic induced contraction pulled out) with portions of the structure being cut-away to more clearly show the construction of the diaper 1900 and with its wearer-facing surface toward the viewer. This diaper is shown for illustration purpose only as the present disclosure may be used for making a wide variety of diapers and other absorbent articles.

Figure 15:
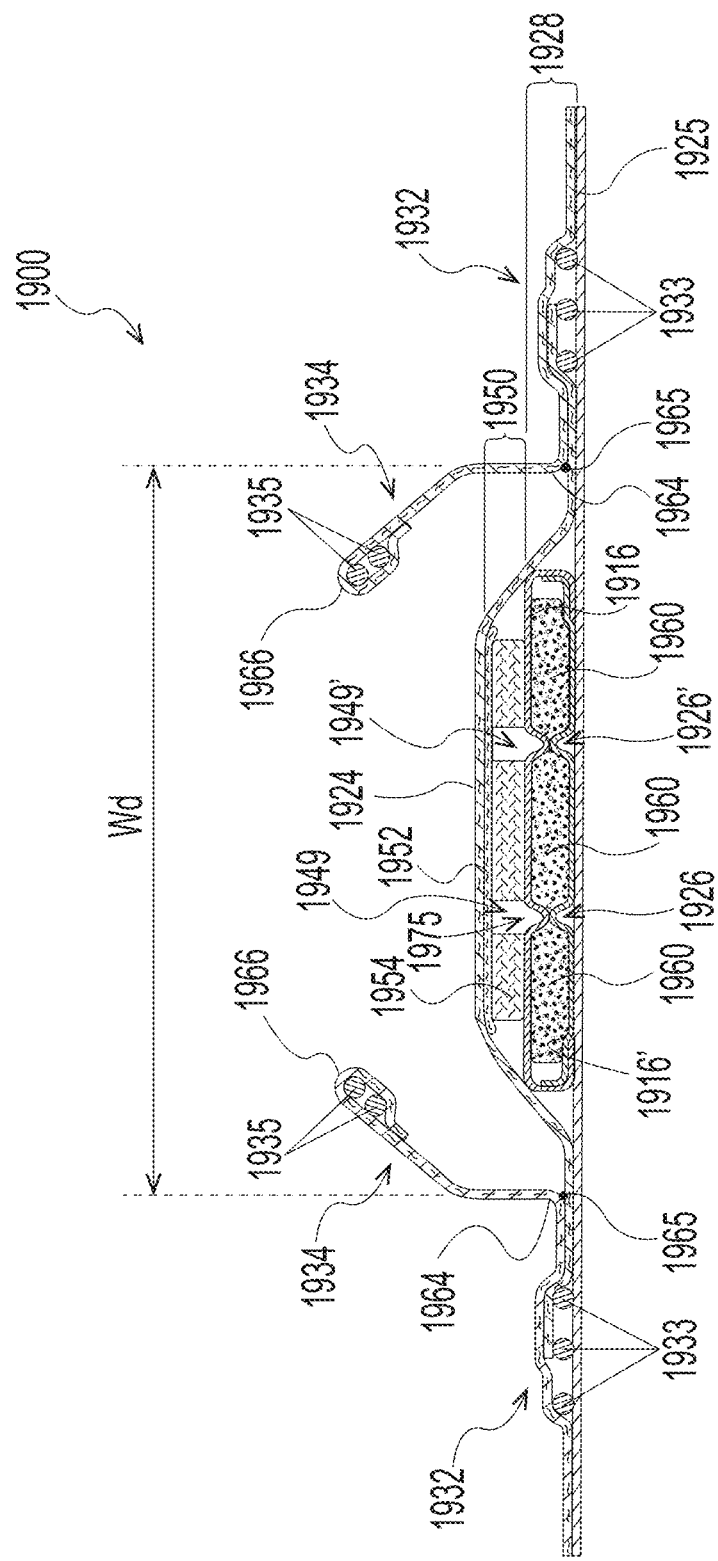
FIG. 15 is a schematic representation of the diaper of FIG. 14 shown in cross section along line 19-19.

The absorbent article may comprise a liquid permeable topsheet 1924, a liquid impermeable backsheet 1925, an absorbent core 1928 positioned at least partially intermediate the topsheet 1924 and the backsheet 1925, and barrier leg cuffs 1934. The absorbent article may also comprise a liquid management system ("LMS") 1950 (shown in FIG. 15), which, in the example represented, comprises a distribution layer 1954 and an acquisition layer 1952 that will both be further discussed below. In various forms, the acquisition layer 1952 may instead distribute bodily exudates and the distribution layer 1954 may instead acquire bodily exudates or both layers may distribute and/or acquire bodily exudates. The LMS 1950 may also be provided as a single layer or two or more layers. The absorbent article may also comprise elasticized gasketing cuffs 1932 joined to the chassis of the absorbent article, typically via the topsheet and/or backsheet, and substantially planar with the chassis of the diaper.

The Figures also show typical taped diaper components such as a fastening system comprising adhesive tabs 1942 or other mechanical fasteners attached towards the rear edge of the absorbent article 1900 and cooperating with a landing zone on the front of the absorbent article 1900. The absorbent article may also comprise other typical elements, which are not represented, such as a rear elastic waist feature and a front elastic waist feature, for example.

The absorbent article 1900 may comprise a front waist edge 1910, a rear waist edge 1912 longitudinally opposing the front waist edge 1910, a first side edge 1903, and a second side edge 1904 laterally opposing the first side edge 1903. The front waist edge 1910 is the edge of the absorbent article 1900 which is intended to be placed towards the front of the user when worn, and the rear waist edge 1912 is the opposite edge. Together the front waist edge 1910 and the rear waist edge form waist opening when the absorbent article 1900 is donned on a wearer. The absorbent article 1900 may have a longitudinal axis 1980 extending from the lateral midpoint of the front waist edge 1910 to a lateral midpoint of the rear waist edge 1912 of the absorbent article 1900 and dividing the absorbent article 1900 in two substantially symmetrical halves relative to the longitudinal axis 1980, with article placed flat and viewed from the wearer-facing surface as illustrated FIG. 14. The absorbent article may also have a lateral axis 1990 extending from the longitudinal midpoint of the first side edge 1903 to the longitudinal midpoint of the second side edge 1904. The length L of the absorbent article 1900 may be measured along the longitudinal axis 1980 from the front waist edge 1910 to the rear waist edge 1912. The crotch width of the absorbent article 1900 may be measured along the lateral axis 1990 from the first side edge 1903 to the second side edge 1904. The absorbent article 1900 may comprise a front waist region 1905, a rear waist region 1906, and a crotch region 1907. The front waist region, the rear waist region, and the crotch region each define ⅓ of the longitudinal length of the absorbent article. Front and back portions may also be defined on opposite sides of the lateral axis 1990.

The topsheet 1924, the backsheet 1925, the absorbent core 1928, and the other article components may be assembled in a variety of configurations, in particular by gluing or heat embossing, for example. Example diaper configurations are described generally in U.S. Pat. Nos. 3,860,003, 5,221,274, 5,554,145, 5,569,234, 5,580,411, and 6,004,306.

The absorbent core 1928 may comprise an absorbent material comprising 75% to 100%, at least 80%, at least 85%, at least 90%, at least 95%, or at least 99%, all by weight, of the absorbent material, specifically reciting all 0.1% increments within the above-specified ranges and all ranges formed therein or thereby, and a core wrap enclosing the absorbent material. The core wrap may typically comprise two materials, substrates, or nonwoven materials 16 and 16' for the top side and bottom side of the core. Cores comprising relatively high amount of SAP with various core designs are disclosed in U.S. Pat. No. 5,599,335 (Goldman), EP 1,447,066 (Busam), WO 95/11652 (Tanzer), U.S. Pat. Publ. No. 2008/0312622A1 (Hundorf), and WO 2012/052172 (Van Malderen).

Figure 16:
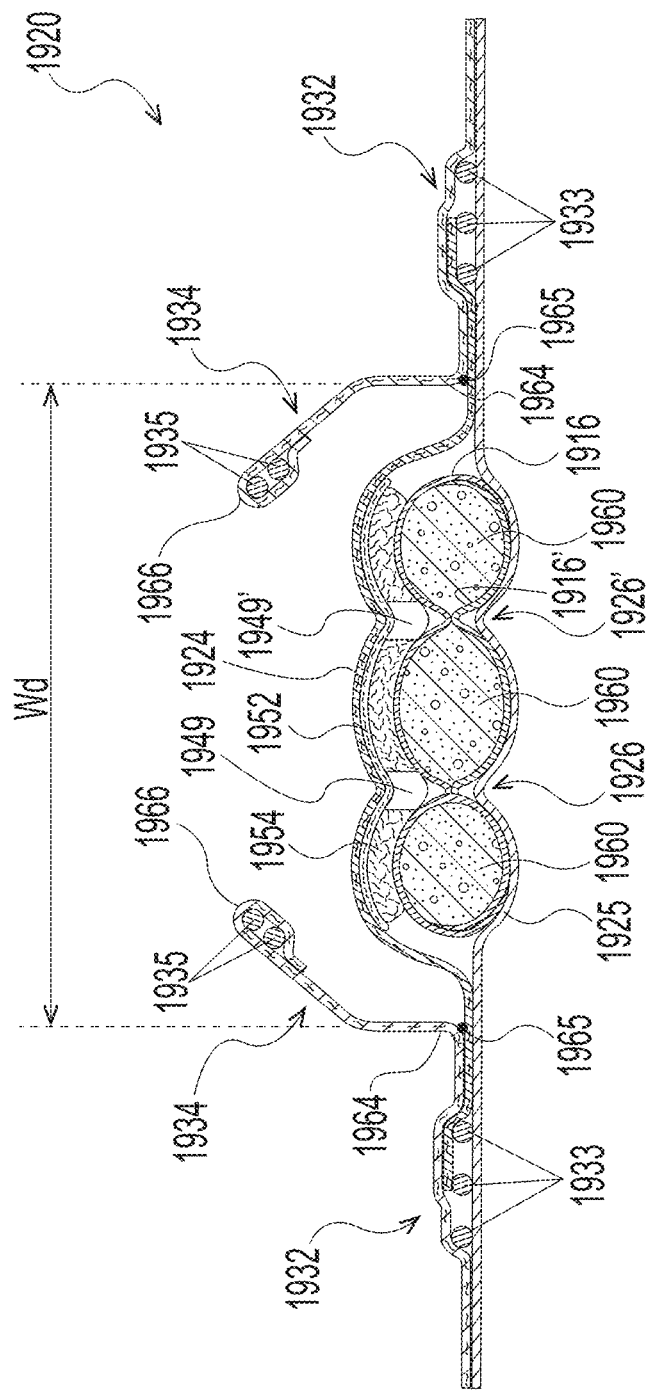
FIG. 16 is a schematic representation of the diaper of FIG. 15 showing the diaper in swelled state.

The absorbent core 1928 may comprises one or more channels, represented in FIG. 14 as the four channels 1926, 1926' and 1927, 1927'. Additionally or alternatively, the LMS 1950 may comprises one or more channels, represented in FIGS. 14-16 as channels 1949, 1949'. In some forms, the channels of the LMS 1950 may be positioned within the absorbent article 1900 such they aligned with, substantially aligned with, overlap, or at least partially overlap, the channels of the absorbent core 1928. These and other components of the absorbent articles will now be discussed in more details.

The topsheet 1924 is the part of the absorbent article that is directly in contact with the wearer's skin. The topsheet 1924 may be joined to the backsheet 1925, the core 1928 and/or any other layers as is known to those of skill in the art. Usually, the topsheet 1924 and the backsheet 1925 are joined directly to each other in some locations (e.g., on or close to the periphery of the article) and are indirectly joined together in other locations by directly joining them to one or more other elements of the absorbent article 1900.

The backsheet 1925 is generally that portion of the absorbent article 1900 positioned adjacent the garment-facing surface of the absorbent core 1928 and which prevents, or at least inhibits, the bodily exudates absorbed and contained therein from soiling articles such as bedsheets and undergarments. The backsheet 1925 is typically impermeable, or at least substantially impermeable, to liquids (e.g., urine, running BM), but permeable to vapors to allow the diaper to "breath". The backsheet may, for example, be or comprise a thin plastic film such as a thermoplastic film having a thickness of about 0.012 mm to about 0.051 mm.

As used herein, the term "absorbent core" refers to the individual component of the absorbent article having the most absorbent capacity and that comprises an absorbent material. The absorbent core may comprise a core wrap or core bag (hereafter "core wrap") enclosing the absorbent material. The term "absorbent core" does not include the LMS or any other component of the absorbent article which is not either integral part of the core wrap or placed within the core wrap. The absorbent core may comprise, consist essentially of, or consist of, a core wrap, absorbent material as defined below, and glue enclosed within the core wrap. Pulp or air-felt may also be present within the core wrap and may form a portion of the absorbent material.

The core wrap may be formed by two nonwoven materials, substrates, laminates, or other materials, 1916, 1916' which may be at least partially sealed along the sides of the absorbent core. The core wrap may be at least partially sealed along its front side, rear side, and two longitudinal sides so that substantially no absorbent material leaks out of the absorbent core wrap. The first material, substrate, or nonwoven 1916 may at least partially surround the second material, substrate, or nonwoven 1916' to form the core wrap. The first material 1916 may surround a portion The absorbent article 1900 may comprise a pair of barrier leg cuffs 1934. Each barrier leg cuff may be formed by a piece of material which is bonded to the absorbent article so it can extend upwards from the inner surface of the absorbent article and provide improved containment of liquids and other bodily exudates approximately at the junction of the torso and legs of the wearer. The barrier leg cuffs 1934 are delimited by a proximal edge 1964 joined directly or indirectly to the topsheet 1924 and/or the backsheet 1925 and a free terminal edge 1966, which is intended to contact and form a seal with the wearer's skin. The barrier leg cuffs 1934 extend at least partially between the front waist edge 1910 and the rear waist edge 1912 of the absorbent article on opposite sides of the longitudinal axis 1980 and are at least present in the crotch region 1907. The barrier leg cuffs 1934 may be joined at the proximal edge 1964 with the chassis of the absorbent article by a bond 1965 which may be made by gluing, fusion bonding, or combination of other suitable bonding processes. The bond 1965 at the proximal edge 64 may be continuous or intermittent. The bond 1965 closest to the raised section of the leg cuffs 1934 delimits the proximal edge 1964 of the standing up section of the leg cuffs 1934.

The barrier leg cuffs 1934 may be integral with the topsheet 1924 or the backsheet 1925 or may be a separate material joined to the absorbent article's chassis. The material of the barrier leg cuffs 1934 may extend through the whole length of the diapers but may be "tack bonded" to the topsheet 1924 towards the front waist edge 1910 and rear waist edge 1912 of the absorbent article so that in these sections the barrier leg cuff material remains flush with the topsheet 1924.

Each barrier leg cuff 1934 may comprise one, two or more elastic strands or strips of film 1935 close to this free terminal edge 1966 to provide a better seal.

In addition to the barrier leg cuffs 1934, the absorbent article may comprise gasketing cuffs 1932, which are joined to the chassis of the absorbent article, in particular to the topsheet 1924 and/or the backsheet 1925 and are placed externally relative to the barrier leg cuffs 1934. The gasketing cuffs 1932 may provide a better seal around the thighs of the wearer. Each gasketing leg cuff may comprise one or more elastic strings 1933 or elastic elements in the chassis of the absorbent article between the topsheet 1924 and backsheet 1925 in the area of the leg openings. All or a portion of the barrier leg and/or gasketing cuffs may be treated with a lotion or skin care composition. The barrier leg cuffs may be constructed in a number of different configurations, including those described in U.S. Pat. App. Publ. No. 2012/0277713.

In a form, the absorbent article may comprise front ears 1946 and rear ears 1940. The ears may be an integral part of the chassis, such as formed from the topsheet 1924 and/or backsheet 1925 as side panel. Alternatively, as represented on FIG. 14, the ears (1946, 1940) may be separate elements attached by gluing, heat embossing, and/or pressure bonding. The rear ears 1940 may be stretchable to facilitate the attachment of the tabs 1942 to the landing zone 1944 and maintain the taped diapers in place around the wearer's waist. The rear ears 1940 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

One function of the LMS 1950 is to quickly acquire the fluid and distribute it to the absorbent core 1928 in an efficient manner. The LMS 1950 may comprise one or more layers, which may form a unitary layer or may remain as discrete layers which may be attached to each other. The LMS 1950 may comprise additional layers: a distribution layer 1954 and/or an acquisition layer 1952 disposed between the absorbent core and the topsheet, but the present disclosure is not limited to such a configuration.

The LMS 1950 may comprise SAP as this may slow the acquisition and distribution of the fluid. In other forms, the LMS may be substantially free (e.g., 80%, 85%, 90%, 95%, or 99% free of) or completely free of SAP. The LMS may also comprise one or more of a variety of other suitable types of materials, such as opened-cell foam, air-laid fibers, or carded, resin bonded nonwoven materials, for example. Suitable example LMSs are described in WO 2000/59430 (Daley), WO 95/10996 (Richards), U.S. Pat. No. 5,700,254 (McDowall), and WO 02/067809 (Grad), for example.

The distribution layer 1954 may comprise at least 50% or more by weight of cross-linked cellulose fibers, for example. Suitable materials for distribution layers are disclosed in U.S. Pat. Publ. No. 2008/0312622 A1 (Hundorf).

The acquisition layer 1952 may be disposed, for example, between the distribution layer 1954 and the topsheet 1924. The acquisition layer 1952 may be or may comprise a non-woven material, such as an SMS or SMMS material, comprising a spunbonded, a melt-blown and a further spunbonded layer or alternatively a carded chemical-bonded nonwoven.

As stated previously, the material webs of the present disclosure may be utilized as a topsheet for a disposable absorbent article, examples of which include the sanitary napkin 1810 and diaper 1900 discussed heretofore.

The material webs of the present disclosure may be used as components of absorbent articles. More than one material web may be used in a single absorbent article. In such a context, the material webs may form at least a portion of: a topsheet; a topsheet and an acquisition layer; a topsheet and a distribution layer; an acquisition layer and a distribution layer; a topsheet, an acquisition layer, and a distribution layer; an outer cover; a backsheet; an outer cover and a backsheet, wherein a film (non-apertured layer) forms the backsheet and a nonwoven web forms the outer cover; a leg cuff; an ear or side panel; a fastener; a waist band; belt or any other suitable portion of an absorbent article. The number of strata in a nonwoven web may also be determined by the nonwoven laminates' particular use.

Additional layers may be positioned between the topsheet and the absorbent core. For example, a secondary topsheet, acquisition layer, and/or distribution layer, each of which are known in the art, may be positioned between the topsheet and the absorbent core of the absorbent article.

Bio-Based Content for Components

Components of the absorbent articles described herein may at least partially be comprised of bio-based content as described in U.S. Pat. Appl. No. 2007/0219521A1. For example, the superabsorbent polymer component may be bio-based via their derivation from bio-based acrylic acid. Bio-based acrylic acid and methods of production are further described in U.S. Pat. Appl. Pub. No. 2007/0219521 and U.S. Pat. Nos. 8,703,450; 9,630,901 and 9,822,197. Other components, for example nonwoven and film components, may comprise bio-based polyolefin materials. Bio-based polyolefins are further discussed in U.S. Pat. Appl. Pub. Nos. 2011/0139657, 2011/0139658, 2011/0152812, and 2016/0206774, and U.S. Pat. No. 9,169,366. Example bio-based polyolefins for use in the present disclosure comprise polymers available under the designations SHA7260™, SHE150™, or SGM9450F™ (all available from Braskem S.A.).

An absorbent article component may comprise a bio-based content value from about 10% to about 100%, from about 25% to about 100%, from about 40% to about 100%, from about 50% to about 100%, from about 75% to about 100%, or from about 90% to about 100%, for example, using ASTM D6866-10, method B.

Recycle Friendly and Bio-Based Absorbent Articles

Components of the absorbent articles described herein may be recycled for other uses, whether they are formed, at least in part, from recyclable materials. Examples of absorbent article materials that may be recycled are nonwovens, films, fluff pulp, and superabsorbent polymers. The recycling process may use an autoclave for sterilizing the absorbent articles, after which the absorbent articles may be shredded and separated into different byproduct streams. Example byproduct streams may comprise plastic, superabsorbent polymer, and cellulose fiber, such as pulp. These byproduct streams may be used in the production of fertilizers, plastic articles of manufacture, paper products, viscose, construction materials, absorbent pads for pets or on hospital beds, and/or for other uses. Further details regarding absorbent articles that aid in recycling, designs of recycle friendly diapers, and designs of recycle friendly and bio-based component diapers, are disclosed in U.S. Provisional Pat. Appl. No. 62/597,539, filed on Dec. 12, 2017.

Contemplated Combinations

Example A

A absorbent article having a longitudinal axis and a transverse axis which is generally perpendicular to the longitudinal axis, the absorbent article further comprising: a topsheet; a backsheet; an absorbent system disposed between the topsheet and the backsheet; and a material web comprising a film layer and a nonwoven layer, the material web comprising a plurality of first plurality of macro-deformations, a plurality of land areas between adjacent macro-deformations, and a first plurality of micro-deformations disposed in the land areas, wherein each of the first plurality of macro-deformations comprises an open distal end, a second plurality of macro-deformations, each of the second plurality of macro-deformations comprising a distal end, and each distal end comprising a second plurality of micro-deformations, wherein the first plurality of micro-deformations comprises a first average open area and wherein the second plurality of micro-deformations comprises a second average open area, wherein the first average open area is larger than the second average open area.

Example A1

The absorbent article of Example A, wherein the first plurality of micro-deformations forms a portion of a wearer-facing surface of the absorbent article.

Example A2

The absorbent article of any of Examples A-A1, wherein the film layer forms a portion of a wearer-facing surface of the absorbent article.

Example A3

The absorbent article of any of Examples A-A1, wherein the nonwoven layer forms a portion of a wearer-facing surface of the absorbent article.

Example A4

The absorbent article of any of Examples A-A3, wherein the absorbent article further comprises a first zone centrally disposed along the longitudinal axis and a second and third zone flanking the first zone, wherein the first plurality of macro-deformations is comprised by the first zone and the second plurality of macro-deformations is comprised by the second and third zones.

Example A5

The absorbent article of any of Examples A-A4, wherein the material web is a composite.

Example A6

The absorbent article of any of Examples A-A4, wherein the material web is a laminate.

Example A7

The absorbent article of any of Examples A-A6, wherein the first plurality of micro-deformations has an average open area of between 10,000 $\mu m^2$ and about 0.78 $mm^2$, more preferably between 15,000 $\mu m^2$ and about 0.5 $mm^2$, most preferably between about 25,000 $\mu m^2$ and about 0.3 $mm^2$.

Example A8

The absorbent article of any of Examples A-A7, wherein the second plurality of micro-deformations has an average open area of between 500 $\mu m^2$ and about 8,000 $\mu m^2$, more preferably between 1,000 $\mu m^2$ and about 6,000 $\mu m^2$, and most preferably between 1,000 $\mu m^2$ and about 5,000 $\mu m^2$.

Example A9

The absorbent article of any of Examples A-A8, wherein the first plurality of macro-deformations is disposed in a target area.

Example A10

The absorbent article of any of Examples A-A9, wherein the each of the distal ends of the first plurality of macro-deformations comprises an open area of between 0.25 $mm^2$ to about 15 $mm^2$, more preferably between 0.5 $mm^2$ to about 10 $mm^2$, and most preferably from about 1 $mm^2$ to about 5 $mm^2$.

Example B

A absorbent article having a longitudinal axis and a transverse axis which is generally perpendicular to the longitudinal axis, the absorbent article further comprising: a topsheet; a backsheet; an absorbent system disposed between the topsheet and the backsheet; and a material web comprising a film layer and a nonwoven layer, the material web comprising a plurality of first plurality of macro-deformations, each of the first plurality of macro-deformations comprising a first distal end, and wherein each first distal end comprises a first plurality of micro-deformations; a second plurality of macro-deformations, each of the second plurality of macro-deformations comprising a second distal end, and each second distal end comprising a second plurality of micro-deformations, wherein the first plurality of micro-deformations comprises a first average open area and wherein the second plurality of micro-deformations comprises a second average open area, wherein the first average open area is larger than the second average open area.

Example B1

The absorbent article of Example B, wherein the film layer forms a portion of a wearer-facing surface of the absorbent article.

Example B2

The absorbent article of Example B, wherein the nonwoven layer forms a portion of a wearer-facing surface of the absorbent article.

Example B3

The absorbent article of any of Examples B-B2, wherein the absorbent article further comprises a first zone centrally disposed along the longitudinal axis and a second and third zone flanking the first zone, wherein the first plurality of macro-deformations is comprised by the first zone and the second plurality of macro-deformations is comprised by the second and third zones.

Example B4

The absorbent article of any of Examples B-B3, wherein the material web is a composite.

Example B5

The absorbent article of any of Examples B-B3, wherein the material web is a laminate.

Example B6

The absorbent article of any of Examples B-B5, wherein the first plurality of micro-deformations has an average open area of between 10,000 $\mu m^2$ and about 7.0 $mm^2$, more preferably between 15,000 $\mu m^2$ and about 5.0 $mm^2$, most preferably between about 25,000 $\mu m^2$ and about 3.0 $mm^2$.

Example B7

The absorbent article of any of Examples B-B6, wherein the second plurality of micro-deformations has an average open area of less than about 8,000 $\mu m^2$, more preferably less than about 6,000 $\mu m^2$, and most preferably less than about 5,000 $\mu m^2$.

Example B8

The absorbent article of any of Examples B-B7, wherein the first plurality of macro-deformations is disposed in a target area.

Example C

A method of making an absorbent article comprising the steps of: obtaining a film web and a nonwoven composite or laminate; forming a first plurality of micro-deformations; simultaneously forming a first plurality macro-deformations and a second plurality of macro-deformations, wherein each of the first plurality of macro-deformations comprises a first distal end, and wherein each of the second plurality of macro-deformations comprises a second distal end, wherein the first distal ends are configured differently than the second distal ends; obtaining a backsheet web and an absorbent core web; combining the nonwoven composite or laminate with the backsheet web and absorbent core web, cutting the combined nonwoven composite or laminate, absorbent core, and backsheet web, into individual absorbent articles.

Example D

A method of making an absorbent article comprising the steps of: obtaining a film having a first plurality of micro-deformations; a first plurality macro-deformations and a second plurality of macro-deformations, wherein each of the first plurality of macro-deformations comprises a first distal end, and wherein each of the second plurality of macro-deformations comprises a second distal end, wherein the first distal ends are configured differently than the second distal ends; laminating the film with a nonwoven web; obtaining a backsheet web and an absorbent core web; combining the nonwoven composite or laminate with the backsheet web and absorbent core web, cutting the combined nonwoven and film, absorbent core, and backsheet web, into individual absorbent articles.

Example E

A method of making an absorbent article comprising the steps of: obtaining a film/nonwoven laminate or composite having a first plurality of micro-deformations; a first plurality macro-deformations and a second plurality of macro-deformations, wherein each of the first plurality of macro-deformations comprises a first distal end, and wherein each of the second plurality of macro-deformations comprises a second distal end, wherein the first distal ends are configured differently than the second distal ends; laminating the film with a nonwoven web; obtaining a backsheet web and an absorbent core web; combining the nonwoven composite or laminate with the backsheet web and absorbent core web, cutting the combined nonwoven and film, absorbent core, and backsheet web, into individual absorbent articles.

Example F

A disposable absorbent article having a longitudinal axis and a transverse axis which is generally perpendicular to the longitudinal axis, the absorbent article further comprising: a topsheet; a backsheet; an absorbent system disposed between the topsheet and the backsheet; and a material web comprising a film layer and a nonwoven layer, the material web comprising a plurality of macro-deformations, each of the plurality of macro-deformations comprising a distal end, wherein each distal end is open or partially open, a first plurality of micro-deformations, wherein the disposable absorbent article further comprises a first zone and a pair of outer zones flanking the first zone, wherein the first plurality of micro-deformations are disposed in the first zone and the outer zones, and wherein the macro-deformations are disposed in the first zone but not the outer zones.

Example F1

The disposable absorbent article of Example F, further comprising a plurality of embossments, wherein the plurality of embossments is disposed in the outer zones.

Example F2

The disposable absorbent article of Examples F-F1, wherein the plurality of embossments is disposed only in the outer zones.

Example G

A disposable absorbent article having a longitudinal axis and a transverse axis which is generally perpendicular to the longitudinal axis, the absorbent article further comprising: a topsheet; a backsheet; an absorbent system disposed between the topsheet and the backsheet; and a material web comprising a film layer and a nonwoven layer, the material web comprising a first plurality of macro-deformations, each of the first plurality of macro-deformations comprising a first distal end, wherein each first distal end is open or optionally comprises a first plurality of micro-deformations; a second plurality of macro-deformations, each of the second plurality of macro-deformations comprising a second distal end, each of the second distal ends comprising a second plurality of micro-deformations; a plurality of lands disposed between adjacent first plurality of macro-deformations and between adjacent second plurality of macro-deformations; and a third plurality of micro-deformations disposed in the plurality of lands, wherein the second plurality of micro-deformations comprise an open area which is less than that of the third plurality of micro-deformations.

Test Methods

Linear distances may be measured by any appropriate instrument that is calibrated and capable of a measurement to the nearest 0.1 mm. Area measurements are made using the projected area of the article, as viewed orthogonally to the plane of the longitudinal and transverse axes, in square millimeters to the nearest 0.1 mm$^2$.

Target Area Test Method

The Target Area Test Method is used to determine the target area length index value and the transverse width of the target area at multiple characteristic points.

A two-dimensional shape, defined by the projection of a planar absorbent article perpendicular to both its longitudinal and transverse axes, is captured and is hereafter referred to as the article projection. The article projection retains the same longitudinal and transverse axes of the article itself. The centroid of the article projection is calculated, and the position of the centroid along the longitudinal axis of the article projection is defined as the article centroid point. A line extending through the article centroid point and parallel to the transverse axis is used to partition the article projection into two sub-shapes, a first article projection and a second article projection. The centroids of the first article projection and second article projection are calculated and defined as the first centroid and second centroid, respectively. The position of the first centroid along the longitudinal axis of the article projection is defined as the first article centroid point. The position of the second centroid along the longitudinal axis of the article projection is defined as the second article centroid point.

Lines extending through the first and second centroid points parallel to the transverse axis of the article projection delineate the front and rear boundaries of the target area. The length of the target area along the longitudinal axis is calculated and reported to the nearest 0.1 mm.

The target area length index value is calculated by dividing the length of the target area by the total length of the core projection along the longitudinal axis and is a dimensionless ratio reported to the nearest 0.01.

The transverse width of the article projection is measured at the front centroid point and rear centroid point and each is reported to the nearest 0.1 mm. The transverse width of the article projection is measured at the narrowest point within the target area and reported to the nearest 0.1 mm.

All measures are performed on five substantially similar absorbent cores and reported as the arithmetic mean of the five values.

Fiber-Fiber Distance Measurement

Z-direction distances between individual fibers in a nonwoven layer in a laminate sample having a film layer and a nonwoven layer is measured using micro-CT fiber-to-fiber distance measurement based on analysis of a 3D x-ray image of a sample obtained on a micro-CT instrument having a cone beam microtomograph with a shielded cabinet such as Scanco μCT 50 (Scanco Medical AG, Switzerland) and equivalents. A maintenance free x-ray tube is used as the source with an adjustable diameter focal spot. The x-ray beam passes through the sample, where some of the x-rays are attenuated by the sample. The extent of attenuation correlates to the mass of material the x-rays have to pass through. The transmitted x-rays continue on to the digital detector array and generate a 2D projection image of the sample. Multiple individual projection images of the sample, generated as it is rotated, are collected and then reconstructed into a single 3D image. The instrument is interfaced with a computer running software to control the image acquisition and reconstruction of the raw data into a 3D image. The 3D image is then analyzed using image analysis software such as MATLAB (The Mathworks, Inc., MA, USA) and Avizo Lite (Visualization Sciences Group/FEI Company, MA, USA) and equivalents to identify and segment out the film layer from the nonwoven layer, and measure Z-direction distances between individual fibers in the nonwoven portion of the laminate sample.

Sample Preparation:

To obtain a sample for measurement, lay a film-nonwoven laminate out flat and die cut a circular piece with a diameter of 7 mm. If the laminate is a component of an absorbent article, tape the absorbent article to a rigid flat surface in a planar configuration, and carefully separate the laminate from the other components of the absorbent article. A scalpel and/or cryogenic spray such as Cyto-Freeze (Control Company, TX, USA) can be used to remove the laminate from the other components of the absorbent article, if necessary, to avoid extension of the laminate. Once the laminate has been removed from the article, proceed with die cutting the sample as described above.

A sample may be cut from any location containing the laminate to be analyzed. When selecting a location for sampling, care should be taken to avoid embossed regions, if any, in the absorbent article where the laminate may have been crushed and/or compressed during the article making process, as well as any folds, wrinkles or tears.

Image Acquisition:

The micro-CT instrument is set up and calibrated according to the manufacturer's specifications. The sample is placed into an appropriate holder, between two rings of a low density material, such as foam, which have an inner diameter of at least 4 mm. This allows the central region of the sample to lay horizontal and be scanned without having any other materials directly adjacent to its upper and lower surfaces. Analysis is performed within this central region. A single 3D dataset of contiguous 3 μm isotropic voxels is collected. The 3D dataset is centered on the central analysis region, having dimensions of 7 mm on each side in the XY-plane and a sufficient number of slices to fully include the Z-direction of the sample. Images are acquired with the source at 45 kVp and 88 μA with no additional low energy filter. Current and voltage settings may be optimized to produce the maximum contrast in the projection data with sufficient x-ray penetration through the sample, but once optimized held constant for all substantially similar samples. A total of 3200 projection images are obtained with an integration time of 1000 ms and 3 averages. The projection images are reconstructed using acquisition and reconstruction software accompanies the instrument into a 3D dataset having an isotropic spatial resolution of 3 μm, and saved in 16-bit RAW format to preserve the full detector output signal for analysis.

Image Processing:

The 3D dataset is loaded into the image analysis software and trimmed to a rectangular prism 3D image of the analysis region by removing the surrounding holder and the low density mounting material from the 3D dataset Trimming is performed such that the maximum amount of the sample in the analysis region is retained in the 3D image, and the empty space above and below the sample is minimized. The trimmed 3D image is scaled from 16-bit to 8-bit for the purpose of convenience in data analysis, and thresholded using Otsu's method which calculates the threshold level that minimizes the weighted intra-class variance, to separate and remove the background signal due to air but maintain the signal from the film and fibers within the sample image. Film and/or fiber containing voxels are referred to as "material" voxels.

A connected components algorithm is executed on the trimmed 3D image, which identifies and groups together any material voxels that are 26-connected (touching one of their faces, edges, or corners) to any neighboring material voxels. Any material voxel clusters containing fewer than 1000 connected voxels are identified as noise and removed from the 3D image.

The 3D image is oriented so that the film upper surface is as close to parallel with the XY-plane as possible.

The film layer is identified and distinguished from nonwoven fibers using a Z-direction vector, such that given an XY-plane position, a typical Z-direction vector traveling from the top of the 3D image to the bottom will first pass through the film, and then pass through underlying nonwoven fibers. However, in the regions where apertures formed in the film layer, a fiber may be the first material encountered, and must be distinguished from the film layer. As an individual Z-direction vector travels from the top of the 3D image downward, there may be a series of contiguous material voxels in the vector as it passes through the first material encountered. The last material voxel in this series of contiguous material voxels is identified as a potential lower film surface or "bottom of film" voxel. This process is repeated as a Z-direction vector is passed through every XY-plane position in the 3D image, and all of the potential bottom of film voxels are identified. A connected components algorithm is once again executed on only the identified potential bottom of film voxels in the 3D image, which groups together potential bottom film voxels that are 26-connected (touching one of their faces, edges, or corners) to neighboring potential bottom of film voxels. The lower surface of the film is identified as the single largest continuous cluster of potential bottom of film voxels.

The fiber-to-fiber distance is measured along the Z-direction vectors, below the identified lower surface of the film layer from where one fiber ends to the beginning of the next underlying fiber. If no film voxel was identified in the Z-direction vector, due to a hole or aperture in the film layer, any distance measurements from that vector are ignored. Any Z-direction vectors which do not encounter any fibers are also ignored. The median fiber-to-fiber distance of all the distance measurements in the 3D image is calculated and recorded to the nearest 0.1 µm. A total of three substantially similar replicate film-nonwoven laminate samples are analyzed in like manner, and the average of the three recorded median fiber-to-fiber distances is reported to the nearest 0.1 µm.

Distal End Aperture Area Measurement Method

The average distal end aperture area for films having macro-deformations is determined by image analysis of scanning electron microscope images of a representative sample of a subject film material. Images from at least three differing areas of the film sample are obtained and analyzed, providing at least a total of 50 individual distal end aperture area measurements. The film sample is mounted in a planar configuration and gold sputter coated. A top surface plan view of the sample is imaged, such that the plane of the material is generally oriented orthogonal to the viewing angle. The image is obtained at 30× magnification, with a field of view at least 5 mm by 5 mm, with sufficient resolution to visualize and measure the areas of individual distal end apertures. The distal end apertures are identified, segmented from the surrounding region, and their individual areas measured and recorded using appropriate image analysis software. The arithmetic average of the measured distal end aperture areas is reported to the nearest 1 µm$^2$.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a longitudinal axis and a transverse axis which is generally perpendicular to the longitudinal axis, the absorbent article further comprising:
   a topsheet;
   a backsheet; and
   an absorbent system disposed between the topsheet and the backsheet,
   wherein the topsheet comprises a material web comprising a film layer and a nonwoven layer, the material web comprising a surface, a plurality of vacuum-formed micro-apertures having an average open area, and a plurality of macro-deformations formed via mechanical deformation, wherein each of the plurality of macro-deformations comprises a sidewall extending in a Z-direction away from the surface and a distal end, wherein the distal end is partially open such that a portion of the distal end comprises a first subplurality of the micro-apertures, wherein the sidewall comprises a second subplurality of the micro-apertures that have been expanded but not ruptured via stretching, and wherein one of the first subplurality of micro-apertures and the second subplurality of micro-apertures has a larger average open area than the other subplurality of micro-apertures.

2. The absorbent article of claim 1, wherein the film layer forms a portion of a wearer-facing surface of the absorbent article.

3. The absorbent article of claim 1, wherein the nonwoven layer forms a portion of a wearer-facing surface of the absorbent article.

4. The absorbent article of claim 1, wherein the absorbent article further comprises a first zone centrally disposed along the longitudinal axis, and a second and third zone flanking the first zone, wherein the plurality of macro-deformations is located in the first zone.

5. The absorbent article of claim 1, wherein the material web is a composite.

6. The absorbent article of claim 1, wherein the material web is a laminate.

7. The absorbent article of claim 1, wherein the distal end has an open area, wherein the open area is less than about 90 percent.

8. The absorbent article of claim 1, wherein the distal end has an open area, wherein the open area is less than about 75 percent.

9. An absorbent article having a longitudinal axis and a transverse axis which is generally perpendicular to the longitudinal axis, the absorbent article further comprising:
   a topsheet;
   a backsheet; and
   an absorbent system disposed between the topsheet and the backsheet,
   wherein the topsheet comprises a material web comprising a film layer and a nonwoven layer, the material web comprising a surface, wherein the topsheet comprises a first zone and a second zone wherein each of the first zone and the second zone comprise a plurality of micro-apertures and wherein the second zone comprises a plurality of macro-deformations comprising a sidewall extending in a Z-direction away from the surface and a distal end, wherein the distal end is partially open such that a portion of the distal end comprises a first subplurality of the micro-apertures, wherein the sidewall comprises a second subplurality of the micro-apertures that have been expanded by stretching, and wherein one of the first subplurality of micro-apertures and the second subplurality of micro-apertures has a larger average open area than the other subplurality of micro-apertures.

* * * * *